United States Patent
Pandey et al.

(10) Patent No.: US 8,124,416 B2
(45) Date of Patent: Feb. 28, 2012

(54) SELECTIVE AND SENSITIVE DETECTION OF MERCURIC ION BY NOVEL DANSYL-APPENDED CALIX[4] ARENE MOLECULES, VIA FLUORESCENCE QUENCHING

(75) Inventors: Siddharth Pandey, New Delhi (IN); Har Mohindra Chawla, New Delhi (IN)

(73) Assignee: Indian Institute of Technology Delhi, New Delhi (IN)

( * ) Notice: Subject to any disclaimer, the term of this patent is extended or adjusted under 35 U.S.C. 154(b) by 121 days.

(21) Appl. No.: 12/620,126

(22) Filed: Nov. 17, 2009

(65) Prior Publication Data

US 2011/0117657 A1    May 19, 2011

(51) Int. Cl.
*G01N 33/20*    (2006.01)
*C07C 309/33*   (2006.01)
*C07C 303/02*   (2006.01)

(52) U.S. Cl. .................... 436/81; 548/305.4; 548/108

(58) Field of Classification Search .................... 436/81; 548/305.4, 108; 558/47
See application file for complete search history.

(56) References Cited

OTHER PUBLICATIONS

Böhmer, V., "Calixarenes, Macrocycles with (Almost) Unlimited Possibilities," *Angew. Chem. Int. Ed. Engl.* 1995, 34, pp. 713-745.

(Continued)

*Primary Examiner* — Vickie Kim
*Assistant Examiner* — Dwan A Gerido
(74) *Attorney, Agent, or Firm* — Foley & Lardner LLP

(57) ABSTRACT

In particular, Compounds of Formula I or Formula II, generally known as calix[4]arenes, may be prepared. The compounds may be used to test samples for the presence of $Hg^{2+}$ by fluorescence quenching. The compounds may also be used to selectively detect $Hg^{2+}$ in samples containing other mono- or divalent metals.

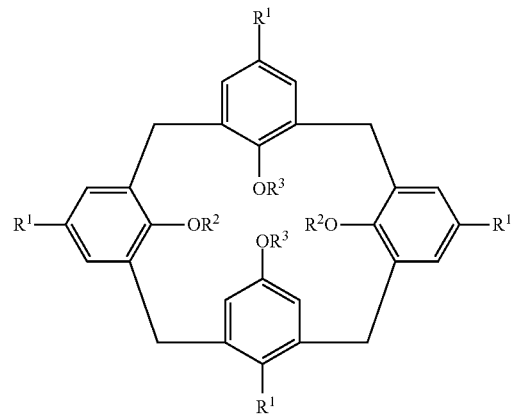

Formula I

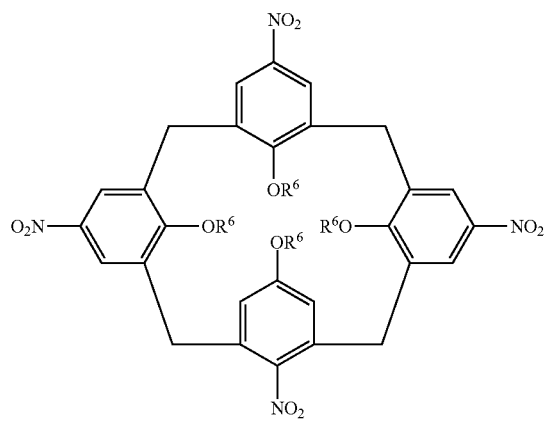

Formula II

19 Claims, 5 Drawing Sheets

OTHER PUBLICATIONS

Métivier, R. et al., "Lead and Mercury Sensing by Calixarene-Based Fluoroionophores Bearing Two or Four Dansyl Fluorophores," *Chem. Eur. J.* 2004, 10, pp. 4480-4490.

Talanova, G. G. et al., "A Calixarene-Based Fluorogenic Reagent for Selective Mercury(II) Recognition," *Analytical Chemistry*, vol. 71, No. 15, Aug. 1, 1999, pp. 3106-3109.

Chawla, H. M. et al., "Synthesis of New Chromogenic Calix[4]arenes Bridged at the Upper Rim through Bisazobiphenyl Linkages," *J. Org. Chem.* 1996, 61, pp. 8464-8467.

Kim, J. S. et al., "Chromogenic Azo-Coupled Calix[4]arenes," *J. Org. Chem.* 2002, 67, pp. 1372-1375.

Doody, M. A. et al., "Affinity and Mobility of Polyclonal Anti-Dansyl Antibodies Sequestered within Sol-Gel-Derived Biogels," *Chem. Mater.* 2000, 12, pp. 1142-1147.

Cardona, C. M. et al., "Dendrimers Functionalized with a Single Fluorescent Dansyl Group Attached "Off Center": Synthesis and Photophysical Studies," *J. Amer. Chem. Soc.*, vol. 122, No. 26, Jul. 5, 2000, pp. 6139-6144.

Pandey, S. et al., "On the Microenvironments Surrounding Dansyl Sequestered within Class I and II Xerogels," *Chem. Mater.* 2000, 12, pp. 3547-3551.

Munson, C. A. et al., "Three-Arm Poly(dimethylsiloxane) Junction Bearing a Single Pendant Dansyl Group: A Model Architecture for Polymer Junction Points Dissolved in Liquids and Molten Polymers," *Macromolecules* 2001, 34, pp. 4624-4629.

Kim, J. S. et al., "Synthesis and Metal Ion Complexation Studies of Proton-Ionizable Calix[4]azacrown Ethers in the 1,3-Alternate Conformation," *J. Org. Chem.* 2000, 65, pp. 2386-2392.

Bügler, J. et al., "Novel Water-Soluble β-Cyclodextrin-Calix[4]arene Couples as Fluorescent Sensor Molecules for the Detection of Neutral Analytes," *J. Org. Chem.* 1998, 63, pp. 5339-5344.

Chawla, H. M. et al., "Synthesis of calix[4]arene(amido)monocrowns and their photoresponsive derivatives," *Tetrahedron* 62 (2006), pp. 9758-9768.

Chen, Q-Y. et al., "A new $Hg^{2+}$-selective fluorescent sensor based on a dansyl amide-armed calix[4]-aza-crown," *Tetrahedron Letters* 46 (2005), pp. 165-168.

Liu, S-y. et al., "Fluorescent sensors for amino acid anions based on calix[4]arenes bearing two dansyl groups," *Tetrahedron Asymmetry* 16 (2005), pp. 1527-1534.

Inouye, M. et al., "Nondestructive Detection of Acetylcholine in Protic Media: Artificial-Signaling Acetylcholine Receptors," *J. Am. Chem.. Soc.* 1994, 116, pp. 5517-5518.

Jin, T. et al., "A Fluorescent Calix[4]arene as an Intramolecular Excimer-forming $Na^+$ Sensor in Nonaqueous Solution," *J. Chem. Soc., Chem. Commun.*, 1992, pp. 499-501.

Kumar, S. et al, "A Convenient One Pot One Step Synthesis of p-Nitrocalixarenes Via Ipsonitration," *Synthetic Communications*, 31(5), (2001), pp. 775-779.

Kumar, S. et al., "Preparation of p-nitrocalix[n]arene methyl ethers via ipso-nitration and crystal structure of tetramethoxytetra-p-nitrocalix[4]arene," *Tetrahedron* 60 (2004), pp. 1001-1005.

Lee, J. Y. et al., "Bifunctional Fluorescent Calix[4]arene Chemosensor for Both a Cation and an Anion," *J. Org. Chem.* 2005, vol. 70, No. 4, pp. 1463-1466.

Munson, C. A. et al., "Effects of Fluid Density on a Poly(dimethylsiloxane)-Based Junction in Pure and Methanol-Modified Carbon Dioxide," *Macromolecules* 2005, 38, pp. 1341-1348.

Nolan, E. M. et al., "Tools and Tactics for the Optical Detection of Mercuric Ion," *Chem. Rev.* 2008, 108, pp. 3443-3480.

Page, P. M. et al., "Comparison of Dansylated Aminopropyl Controlled Pore Glass Solvated by Molecular and Ionic Liquids," *Langmuir* 2007, 23, pp. 843-849.

Pandey, S. et al., "Quenching of Pyrene Fluorescence by Calix[4]arene and Calix[4]resorcinarenes," *J. Fluoresc.* (2008) 18, pp. 533-539.

Souchon, V. et al., "Selective detection of cesium by a water-soluble fluorescent molecular sensor based on a calix[4]arene-bis(crown-6-ether)," *Chem. Commun.*, 2006, pp. 4224-4226.

Valeur, B. et al., "Ion-responsive supramolecular fluorescent systems based on multichromophoric calixarenes: A review," *Inorganica Chimica Acta* 360 (2007), pp. 765-774.

Wosnick, J. H. et al., "Enhanced fluorescence quenching in receptor-containing conjugated polymers: a calix[4]arene-containing poly(phenylene ethynylene)," *Chem. Commun.*, 2004, pp. 2744-2745.

Aoki, I. et al., "A New Metal Sensory System Based on Intramolecular Fluorescence Quenching on the Ionophoric Calix[4]arene Ring," *J. Chem. Soc., Chem.. Commun.*, 1992, pp. 730-732.

Bhalla, V. et al., "Bifunctional fluorescent thiacalix[4]arene based chemosensor for $Cu^{2+}$ and $F^-$ ions," *Tetrahedron* 63 (2007), pp. 11153-11159.

Creaven, B. S. et al., "Unusual cone conformation retention in calix[4]arenes," *Tetrahedron* 57 (2001), pp. 8883-8887.

Fletcher, K. A. et al., "Behavior of the solvatochromic probes Reichardt's dye, pyrene, dansylamide, Nile Red and 1-pyrenecarbaldehyde within the room-temperature ionic liquid $bmimPF_6$," *Green Chemistry*, 2001, 3, pp. 210-215.

Gutsche, C. D. et al., "Calixarenes. 18. Synthesis Procedures for p-tert-Butylcalix[4]arene," *J. Org. Chem.* 1986, 51, pp. 742-745.

Jamie, C. et al., "C NMR Chemical Shifts. A Single Rule to Determine the Conformation of Calix[4]arenes," *J. Org. Chem.* 1991, 56, pp. 3372-3376.

Kim, J. S. et al., "Metal Ion Sensing Novel Calix[4]crown Fluoroionophore with a Two-Photon Absorption Property," *J. Org. Chem.* 2006, 71, pp. 8016-8022.

Kim, J. S. et al., "Calixarene-Derived Fluorescent Probes," *Chem. Rev.* 2007, 107, pp. 3780-3799.

Lalor, R. et al., "Cellular Uptake of a Fluorescent Calix[4]arene Derivative," *J. Am. Chem.. Soc.* 2008, 130, pp. 2892-2893.

Lee, M. H. et al., "Ion-Induced FRET On-Off in Fluorescent Calix[4]arene," *J. Org. Chem.* 2007, 72, pp. 4242-4245.

Othman, A. B. et al., "Calix[4]arene-Based, $Hg^{2+}$-Induced Intramolecular Fluorescence Resonance Energy Transfer Chemosensor," *J. Org. Chem.* 2007, 72, pp. 7634-7640.

Praveen, L. et al., "A New $Hg^{2+}$-Selective Fluorescent Sensor Based on a 1,3-Alternate Thiacalix[4]arene Anchored with Four 8-Quinolinoloxy Groups," *Inorg. Chem.* 2007, vol. 46, No. 16, pp. 6277-6282.

Sun, X. H. et al., "Phenyl-calix[4]arene-Based Fluorescent Sensors: Cooperative Binding for Carboxylates," *J. Org. Chem.* 2007, 72, pp. 2419-2426.

Talanova, G. G. et al., "Novel fluorogenic calix[4]arene-bis(crown-6-ether) for selective recognition of thallium(I)," *Chem. Commun.*, 2005, pp. 5673-5675.

Verboom, W. et al., "Ipso Nitration of p-tert-Butylcallix[4]arenes," *J. Org. Chem..* 1992, 57, pp. 1313-1316.

Aoyama, Y. et al., "Molecular Recognition. 5. Molecular Recognition of Sugars via Hydrogen-Bonding Interaction with a Synthetic Polyhydroxy Macrocycle," *J. Am. Chem. Soc.* 1989, 111, pp. 5397-5404.

Buie, N. M. et al., "New Fluorogenic Dansyl-Containing Calix[4]arene in the *Partial Cone* Conformation for Highly Sensitive and Selective Recognition of Lead(II)," *Inorg. Chem.* 2008, vol. 47, No. 9, pp. 3549-3558.

Casnati, A. et al., "Synthesis, Complexation, and Membrane Transport Studies of 1,3-Alternate Calix[4]arene-crown-6 Conformers: A New Class of Cesium Selective Ionophores," *J. Am. Chem.. Soc.* 1995, 117, pp. 2767-2777.

Chawla, H. M. et al., "Molecular Diagnostics: Synthesis of New Chromogenic Calix[8]arenes as Potential Reagents for Detection of Amines," *J. Chem. Soc., Chem. Commun.*, 1994, pp. 2593-2594.

González-Benito, J. et al., "Solvent and Temperature Effects on Polymer-Coated Glass Fibers. Fluorescence of the Dansyl Moiety," *Journal of Fluorescence*, vol. 11, No. 4, Dec. 2001, pp. 307-314.

Pandey, S. et al., "Novel dansyl-appended calix[4]arene frameworks: fluorescence properties and mercury sensing," *Org. Biomol. Chem.*, 2009, vol. 7, pp. 269-279; first published as an Advance Article on the web Nov. 18, 2008.

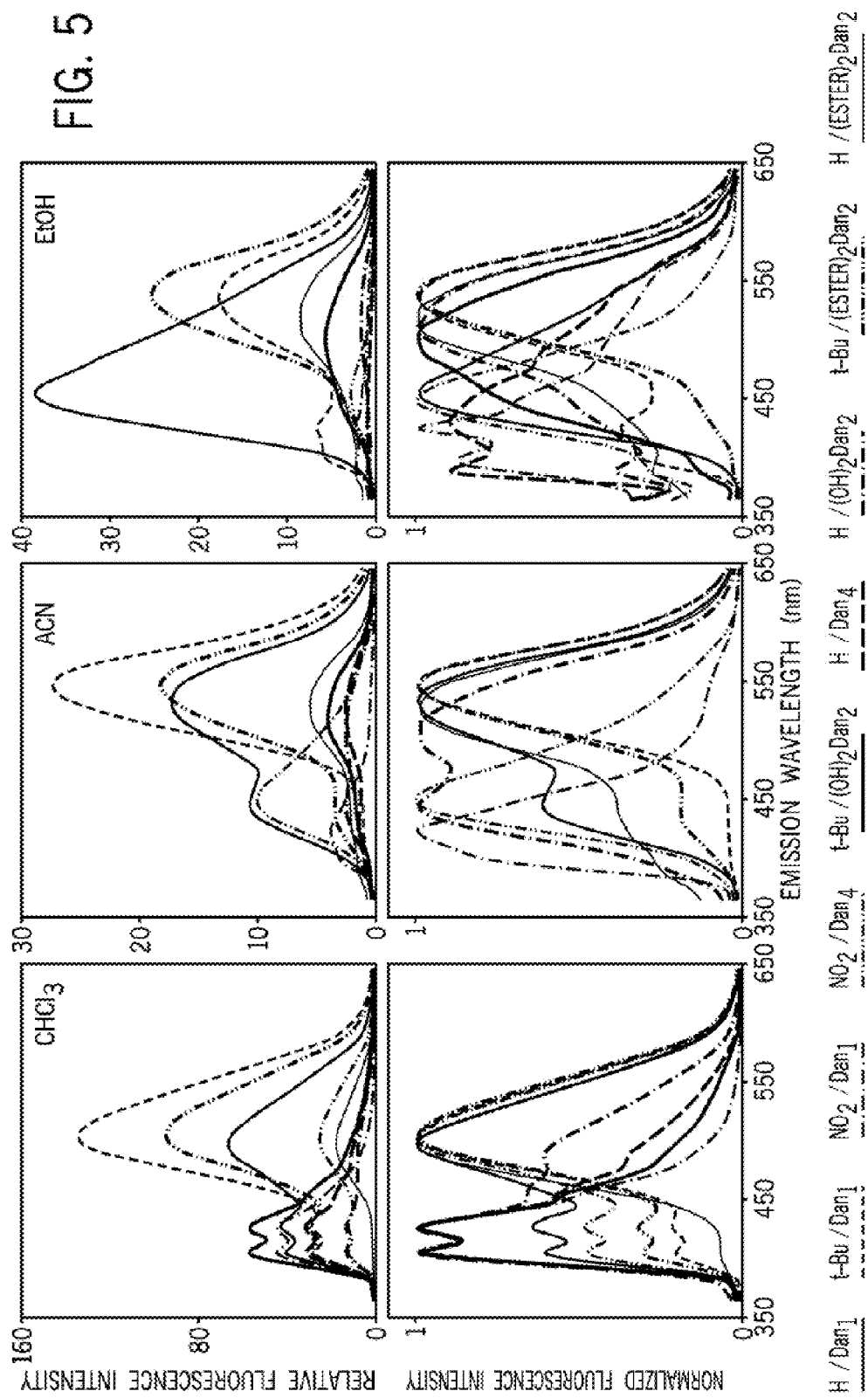

SELECTIVE AND SENSITIVE DETECTION OF MERCURIC ION BY NOVEL DANSYL-APPENDED CALIX[4] ARENE MOLECULES, VIA FLUORESCENCE QUENCHING

TECHNOLOGY

The present technology is related in general metallic ion detection.

BACKGROUND

Mercury pollution is a global problem with respect to the environment and human health. Common contributors to mercury in the environment are fossil fuel combustion, mining operations, and chemical manufacturing. A major source of human exposure to mercury is through the ingestion of contaminated water. In humans and other animals, mercury poisoning results in severe developmental and neurological damage, and death.

Methods for mercury detection include chromatography, electrophoresis and spectroscopy. Small molecule probes and sensors for mercury are available, and are useful in mercury detection by spectrophotometry. The design of novel molecules which can function in various samples and by different mechanisms than those existing, is an area of active research worldwide.

SUMMARY

In one aspect, a compound of Formula I or Formula II is provided. The compounds of Formulas I and II are:

Formula I

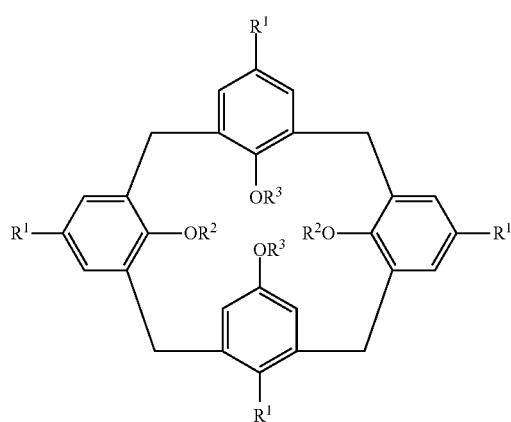

Formula II

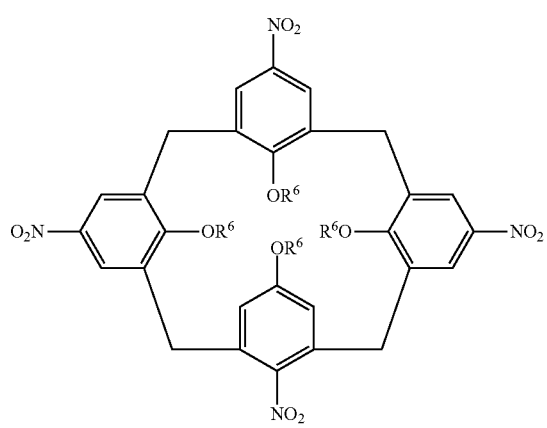

In the above formulas, $R^1$ is H, methyl, ethyl, n-propyl, isopropyl, n-butyl, sec-butyl, tert-butyl, cyclopropyl, cyclobutyl, cyclopentyl or cyclohexyl; $R^2$ is H, $CH_2C(O)OR^4$, or a group of formula

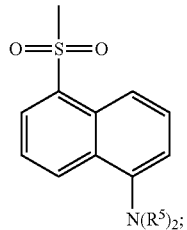

$R^3$ and $R^6$ are individually a group of formula

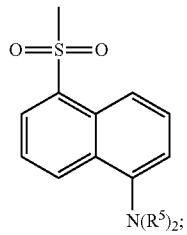

and $R^4$ and $R^5$ are individually methyl, ethyl, n-propyl, isopropyl, n-butyl, sec-butyl, or tert-butyl.

In some embodiments, the compound is of Formula I and $R^1$ is H; $R^2$ is $CH_2C(O)OR^4$; $R^4$ is methyl or ethyl; and $R^5$ is methyl or ethyl. In some embodiments, the compound is of Formula I and $R^1$ is H; $R^2$ is $CH_2C(O)OR^4$; $R^4$ is ethyl; and $R^5$ is methyl. In some other embodiments, the compound is of Formula I and $R^1$ is H; $R^2$ is H; and $R^5$ is methyl. In some embodiments, the compound if of Formula I and $R^1$ is H; $R^2$ is a group of formula

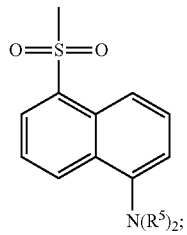

and $R^5$ is methyl. In yet other embodiments, the compound is of Formula I, and $R^1$ is tert-butyl; $R^2$ is $CH_2C(O)OR^4$; $R^4$ is methyl or ethyl; and $R^5$ is methyl or ethyl. In still other embodiments, the compound is of Formula I and $R^1$ is tert-butyl; $R^2$ is $CH_2C(O)OR^4$; $R^4$ ethyl; and $R^5$ is methyl. In yet other embodiments, the compound is of Formula I and $R^1$ is tert-butyl; $R^2$ is H; and $R^5$ is methyl.

In some embodiments, the compound is of Formula II and $R^5$ is methyl or ethyl. In other embodiments, the compound is of Formula II and $R^5$ is methyl.

In another aspect, a complex is provided including the compound of Formula I or Formula II, and a $Hg^{2+}$ ion.

In another aspect, a method is provided for testing for the presence of $Hg^{2+}$. Such methods include detecting the fluorescence of a test sample comprising a compound of Formula I or Formula II, and comparing the detected fluorescence of the test sample to that of a control sample, where a reduction in fluorescence of the test sample relative to the control sample indicates the presence of $Hg^{2+}$ in the sample. In some embodiments, the control sample contains substantially the same amount of the compound as the test sample but lacks $Hg^{2+}$. In other embodiments, the test sample is an aqueous solution. In yet other embodiments, the aqueous solution comprises about 40 to about 75% acetonitrile. In further embodiments, the aqueous solution comprises about 50% acetonitrile. In yet further embodiments, the method selectively detects the presence of $Hg^{2+}$ in the presence of one or more different divalent metal ions in the sample. For example, such divalent metal ions may include $Ca^{2+}$, $Cd^{2+}$, $Co^{2+}$, $Cu^{2+}$, $Fe^{2+}$, $Mg^{2+}$, $Mn^{2+}$, $Ni^{2+}$, $Pb^{2+}$, and $Zn^{2+}$.

In another aspect, a method is provided for testing for the presence of $Hg^{2+}$. Such a method includes preparing a test sample comprising a compound of Formula I or Formula II, detecting the fluorescence of the test sample, and comparing the detected fluorescence of the test sample to that of a control sample, where a reduction in fluorescence of the test sample relative to the control sample indicates the presence of $Hg^{2+}$ in the test sample.

In another aspect, a method of preparing a compound of Formula I includes adding a compound of formula $XSO_2R^3$ to a solution of a compound of Formula III, in the presence of a Lewis base. In such embodiments, the compound of Formula III is Formula III

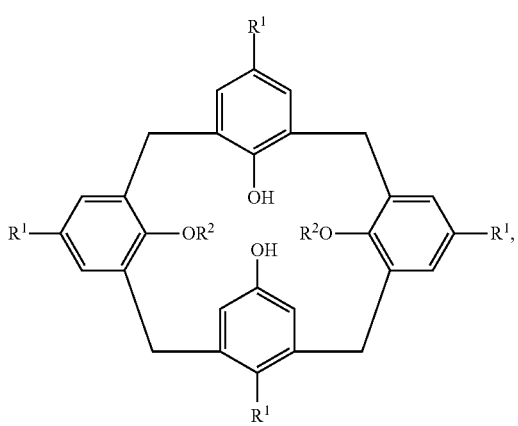

and $R^1$ is H, methyl, ethyl, n-propyl, iso-propyl, n-butyl, sec-butyl, tert-butyl, cyclopropyl, cyclobutyl, cyclopentyl or cyclohexyl; $R^2$ is H, $CH_2C(O)OR^4$, or a group of formula

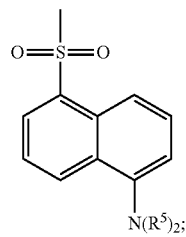

$R^3$ is a group of formula

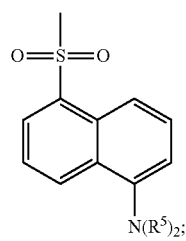

$R^4$ is methyl, ethyl, n-propyl, iso-propyl, n-butyl, sec-butyl, or tert-butyl; and $R^5$ is methyl, ethyl, n-propyl, iso-propyl, n-butyl, sec-butyl, or tert-butyl.

In another aspect, a method of preparing a compound of Formula II includes adding a compound of formula $XSO_2R^3$, where X is F, Cl, Br, or I, and $R^3$ is a group of formula:

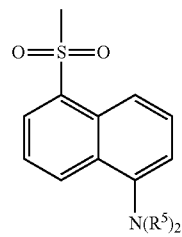

to a solution of a compound of Formula IV, in the presence of a Lewis base, where the compound of Formula IV is:

Formula IV

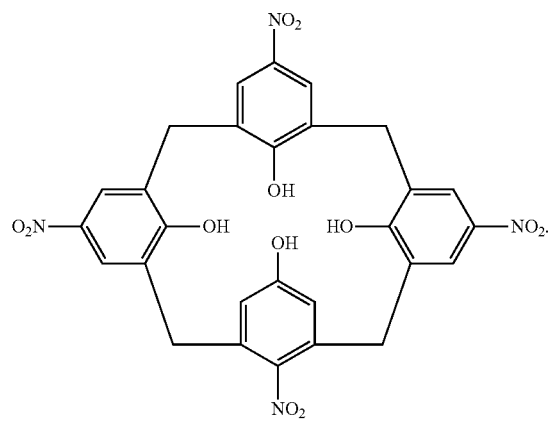

Some embodiments of the methods of preparation, the Lewis base is a tertiary amine or pyridine. In other embodiments of the methods of preparation, the Lewis base is triethylamine, diisopropylethylamine, pyridine, or dimethylaminopyridine.

In some embodiments of the method, the compound is of Formula II, $R^5$ is methyl, and the compound has stereoconformation:

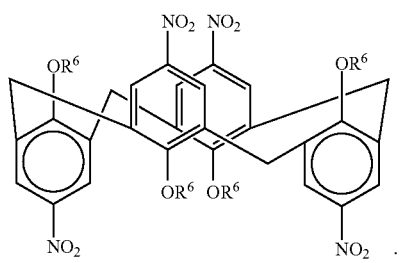

BRIEF DESCRIPTION OF THE DRAWINGS

FIG. 5 illustrates the fluorescence spectra of novel dansyl-appended calyx[4]arenes and three reference compounds in non-polar chloroform (left panels), polar-aprotic acetonitrile (middle panels), and polar-protic ethanol (right panels) at ambient conditions ($\lambda_{excitation}$=351 nm), according to some embodiments. Relative and normalized fluorescence intensities are represented on the y-axis in the upper and lower panels, respectively.

DETAILED DESCRIPTION

Figure 1:
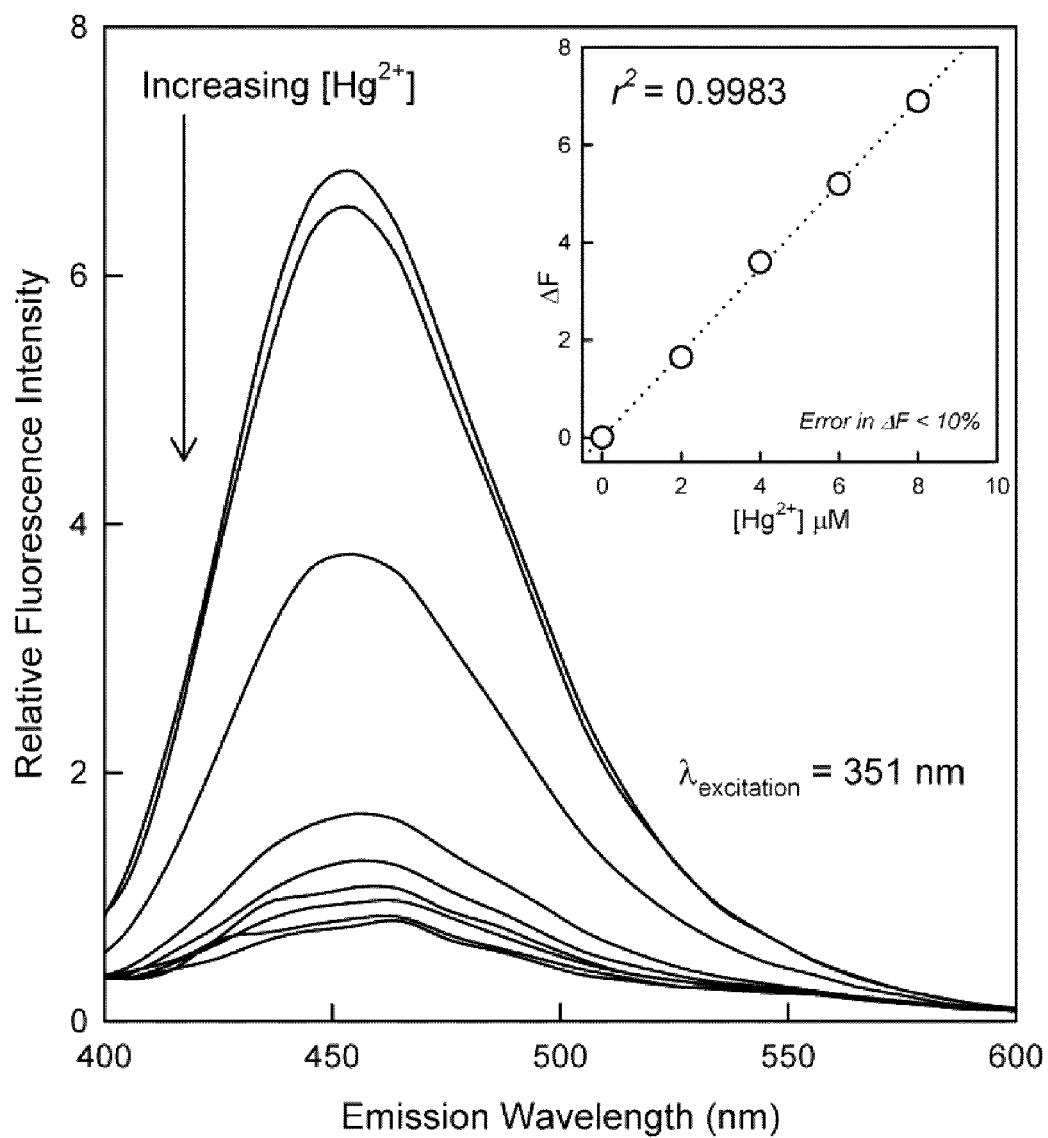
FIG. 1 is a graphic illustration of the quenching of the fluorescence intensity in a compound of Formula II-1 by the presence of $Hg^{2+}$ in acetonitrile at ambient conditions, according to one embodiment. In the graph, the compound is present at $1\times10^{-5}$ M and the excitation wavelength is 351 nm. The inset shows change in fluorescence ($\Delta F$) upon addition of $Hg^{2+}$ for $0 \leq [Hg2+] \leq 8$ μM.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. The present technology is also illustrated by the examples herein, which should not be construed as limiting in any way.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

According to one aspect, the detection of mercury using a selective, and sensitive, chemical sensor is provided.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups.

The terms "cyclic alkyl" or "cycloalkyl" refers to a saturated or partially saturated non-aromatic cyclic alkyl groups of from 3 to 14 carbon atoms and no ring heteroatoms and having a single ring or multiple rings including fused and bridged ring systems. Cycloalkyl or cyclic alkyl groups include mono-, bi- or tricyclic alkyl groups having from 3 to 14 carbon atoms in the ring(s), or, in some embodiments, 3 to 12, 3 to 10, 3 to 8, or 3 to 4, 5, 6 or 7 carbon atoms. Exemplary monocyclic cycloalkyl groups include, but not limited to, cyclopropyl, cyclobutyl, cyclopentyl, cyclohexyl, cycloheptyl, and cyclooctyl groups. Bi- and tricyclic ring systems include both bridged cycloalkyl groups and fused rings, such as, but not limited to, bicyclo[2.1.1]hexane, adamantyl, decalinyl, and the like.

The term "base" refers to a chemical compound that can donate a pair of electrons or donate a hydroxide ion and that can deprotonate another compound when reacted with it. Examples of base include, but are not limited to, tertiary amines, pyridine compounds, sodium and potassium hydroxides, sodium and potassium carbonates, sodium and potassium hydrides, sodium and potassium alkoxides, and the like.

The term "control sample" refers to a sample against which the test sample is compared in order to assess the presence, absence and/or level of analyte in the test sample. As such, in the present methods the control sample may include some or all of the constituents of the test sample, except for the analyte being assessed, e.g., $Hg^{2+}$ ions, or some fixed amount of the analyte. It is within the skill in the art to select the proper control sample for the application at hand based on the present disclosure and knowledge in the art. Depending on the detection method being used, the control sample can be a solid sample or a liquid sample. In some embodiments, the control sample is a liquid.

In a negative control sample, the analyte being assessed, e.g. $Hg^{2+}$ ions, is completely absent. In positive control samples, such as those used for standardization, the sample may contain a known amount of the analyte being assessed.

For comparative measurement of sample fluorescence, the control sample may be dissolved in the same or substantially the same solvent/media as that of the test solvent. By "substantially the same solvent/media" is meant almost but not completely the same solvent/media.

The term "divalent metal ion" refers to any metal ion with a valency of 2. Examples of divalent ions include, but are not limited to, $Hg^{2+}$, $Ca^{2+}$, $Cd^{2+}$, $Co^{2+}$, $Cu^{2+}$, $Fe^{2+}$, $Mg^{2+}$, $Mn^{2+}$, $Ni^{2+}$, $Pb^{2+}$, and $Zn^{2+}$, and the like.

The term "halide" refers to chloro, bromo, fluoro, and iodo.

The term "solvent," as used herein, means a liquid in which a compound is soluble or partially soluble at a given concentration so as to dissolve or partially dissolve the compound. Examples of solvents include, but are not limited to, methanol, ethanol, and acetonitrile. Aqueous solutions of water-soluble solvents may also be used as solvents, e.g., aqueous solutions of methanol, ethanol or acetonitrile.

The term "tertiary amine" refers to a tri-substituted organoamine. Examples of tertiary amines include, but are not limited to, triethylamine, diisopropylethylamine, and the like.

The term "test sample" refers to any sample which is to be tested for the presence and/or concentration of an analyte, such as $Hg^{2+}$ ions. Depending on the detection method being used, the test sample can be a solid sample or a liquid sample. In some embodiments, the test sample is a liquid.

As used herein, the term "dansyl" refers to the following chemical group:

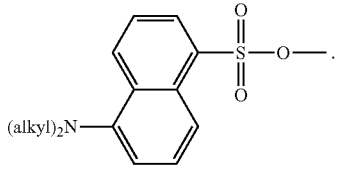

Compounds of the present technology may form salts with inorganic or organic acids. Thus, salts of the present compounds, include but are not limited to, salts of $HClO_4$, HCl, $H_2SO_4$, and $H_3PO_4$, as well as acetic acid or trifluoroacetic acid. Suitable salts include those described in P. Heinrich Stahl, Camille G. Wermuth (Eds.), Handbook of Pharmaceutical Salts Properties, Selection, and Use; 2002.

In one aspect, there is provided a calix[4]arene compound having at least two dansyl groups. The calix[4]arene compounds of the present technology detect mercury ions by a change in their fluorescence emission in solution. Binding of mercury to such calix[4]arene compounds results in a decrease in the fluorescence emission (quenching) of the compounds. It has been found that calix[4]arene compounds containing at least two dansyl groups act as selective sensors for mercury ions.

Accordingly, in some embodiments of the present technology there is provided a compound of Formula I or Formula II:

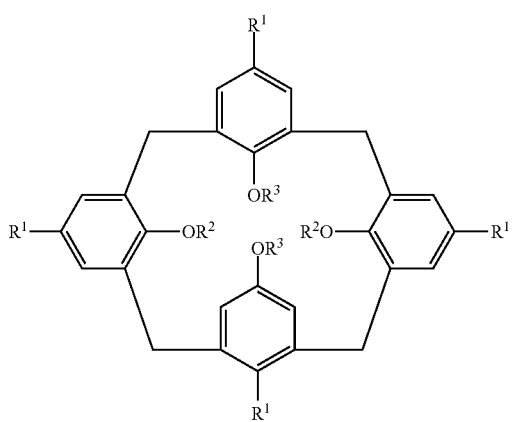

Formula I

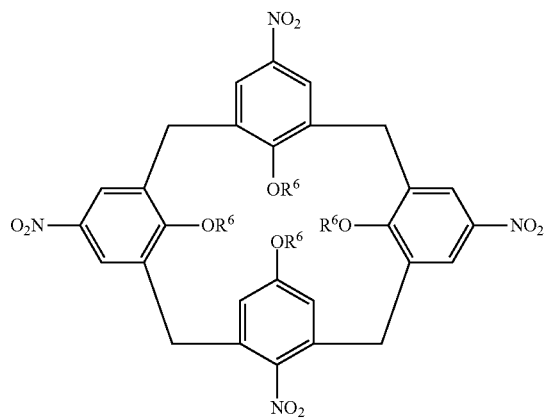

Formula II where $R^1$ is a straight, branched, or cyclic alkyl group; $R^2$ is H, $CH_2C(O)OR^4$ or a group of formula

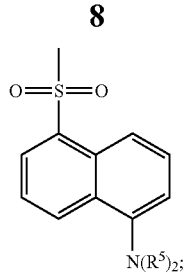

$R^3$ and $R^6$ are individually a group of formula

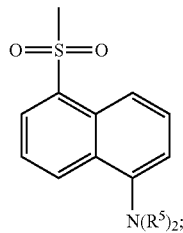

$R^4$ is a straight, branched, or cyclic alkyl group; and $R^5$ is a straight, branched, or cyclic alkyl group.

In some embodiments of the compound of Formula I or Formula II, each $R^1$ is a H, methyl, ethyl, n-propyl, iso-propyl, n-butyl, sec-butyl, tert-butyl, cyclopropyl, cyclobutyl, cyclopentyl or cyclohexyl group. In some embodiments of the compound of Formula I or Formula II, each $R^4$ and $R^5$ is individually a methyl, ethyl, n-propyl, iso-propyl, n-butyl, sec-butyl, tert-butyl, cyclopropyl, cyclobutyl, cyclopentyl or cyclohexyl group. In some embodiments, the compound is of Formula I and $R^1$ is H; $R^2$ is $CH_2C(O)OR^4$; $R^4$ is methyl or ethyl; and $R^5$ is methyl or ethyl. In some other embodiments, the compound is of Formula I and $R^1$ is H; $R^2$ is $CH_2C(O)OR^4$; $R^4$ ethyl; and $R^5$ is methyl. In other embodiments, the compound is of Formula I and $R^1$ is H; $R^2$ is H, and $R^5$ is methyl. In other embodiments, the compound is of Formula I and $R^1$ is H; $R^2$ is a group of formula

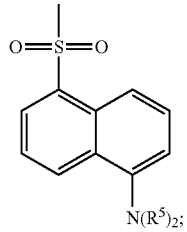

and $R^5$ is methyl. In yet other embodiments, the compound is of Formula I, and $R^1$ is tert-butyl; $R^2$ is $CH_2C(O)OR^4$; $R^4$ is methyl or ethyl; and $R^5$ is methyl or ethyl. In still other embodiments, the compound is of Formula I and $R^1$ is tert-butyl; $R^2$ is $CH_2C(O)OR^4$; $R^4$ ethyl; and $R^5$ is methyl. In still other embodiments, the compound is of Formula I and $R^1$ is tert-butyl; $R^2$ is H; and $R^5$ is methyl.

In some embodiments, the compound is of Formula II and $R^5$ is methyl or ethyl. In other embodiments, the compound is of Formula II and $R^5$ is methyl. In some embodiments, the compound is of Formula II, $R^5$ is methyl, and it has the following stereochemical conformation:

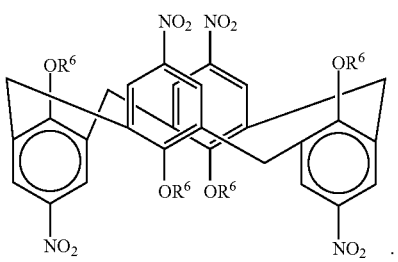

In another aspect, there are provided complexes including a compound as disclosed herein (e.g., compounds of Formula I or Formula II) and a $Hg^{2+}$ ion. In some embodiments, the complex includes a $Hg^{2+}$ ion and a compound I-1, according to Table 1. In some embodiments, the complex includes a $Hg^{2+}$ ion and a compound I-2, according to Table 1. In some embodiments, the complex includes a $Hg^{2+}$ ion and a compound I-3, according to Table 1. In some embodiments, the complex includes a $Hg^{2+}$ ion and a compound I-4, according to Table 1. In some embodiments, the complex includes a $Hg^{2+}$ ion and a compound I-5, according to Table 1. In some embodiments, the complex includes a $Hg^{2+}$ ion and a compound II-1, according to Table 1.

TABLE 1

Example compounds of Formula I and Formula II:

| Formula | R-Groups |
|---|---|
| I-1 | $R^1$ is H; $R^2$ is $CH_2C(O)OR^4$; $R^4$ is ethyl; and $R^3$ is a dansyl group where the alkyl is methyl. |
| I-2 | $R^1$ is H; $R^2$ is H; and $R^3$ is a dansyl group where the alkyl is methyl. |
| I-3 | $R^1$ is H; and $R^2$ and $R^3$ are dansyl groups where the alkyl is methyl. |
| I-4 | $R^1$ is tert-butyl; $R^2$ is $CH_2C(O)OR^4$; $R^4$ is ethyl; and $R^3$ is a dansyl group where the alkyl is methyl. |
| I-5 | $R^1$ is tert-butyl; $R^2$ is H; and $R^3$ is a dansyl group where the alkyl is methyl. |
| II-1 | $R^6$ is a dansyl group where the alkyl is methyl. |

In some embodiments, the complex is a 2:1 complex between a compound of Formula I or Formula II and a $Hg^{2+}$ ion.

In another aspect of the present technology, there are provided methods of testing for the presence of $Hg^{2+}$ ions in a sample using the calix[4]arenes disclosed herein. In some embodiments, the methods include: detecting the fluorescence of a test sample including a compound of Formula I or Formula II; and comparing the detected fluorescence of the test sample to that of a control sample, wherein a reduction in fluorescence of the sample relative to the control sample indicates the presence of $Hg^{2+}$ in the test sample. According to various embodiments, the compound of Formula I or II is compound of Formula I-1, I-2, I-3, I-4, I-5, or II-1, according to Table 1.

The methods of the present technology can be used to detect the presence of low levels of $Hg^{2+}$ ions in any test sample. In some embodiments, the test sample is a biological sample including, but not limited to, blood, cells, tissue, saliva, sweat, extracts of any of the foregoing, and the like. In some embodiments, the test sample is a nutritional sample including, but not limited to, a drink, food (including but not limited to fish and other animals eaten by humans), and extracts thereof. In some embodiments, the test sample is an environmental sample including, but not limited to, water (including surface water or underground water), and extracts and filtrates of air, soil, sediment, clay, and the like. In some embodiments, the test sample is taken from or prepared from a building where people live or work, including paint or other surface coatings, floors, walls, ceilings, furniture, toys, appliances, plumbing and plumbing fixtures (including water from water storage tanks or water heaters), and the like. Test samples may also be prepared from the aforementioned sources by use of standard techniques such as acid digestion and extraction to isolate in whole or part, the mercury to be analyzed from the rest of the sample source.

In some embodiments, the present methods include preparing the test samples by, e.g., combining a compound of Formula I or II, with the test sample prior to detecting the fluorescence of the sample. The compound of Formula I or II and the test sample may be combined in several ways. In some embodiments, the compound of Formula I or II may be added to the test sample as a solid or as a solution (e.g., in an organic solvent such as chloroform or acetonitrile or methanol, or aqueous organic solutions such as aqueous methanol or aqueous acetonitrile). Alternatively, the test sample or an aliquot thereof may be added to the compound of Formula I or II or to a solution thereof. The test sample may also be prepared by adding the compound of Formula I or II or a solution thereof and an aliquot of the sample to be tested to a third solution.

In some embodiments of the present methods, the compound of Formula I or II and the test sample can both be dissolved in the same solvent or different solvents prior to the fluorescence studies. In some embodiments, the compound of Formula I or II and the test sample can be dissolved in solvents such as water, alcohol, acetonitrile and the like or combinations thereof. In some embodiments, the test sample and/or the control sample is an aqueous solution. In some embodiments, the test sample may be prepared by dissolving the sample to be analyzed in an aqueous solution including water in combination with water-miscible solvents. In some embodiments, the sample to be analyzed is dissolved in an aqueous solution including water with acetonitrile or methanol. In some embodiments, the sample to be analyzed is dissolved in an aqueous acetonitrile solution. In some embodiments, the aqueous sample solution includes about 10% to about 90% acetonitrile (by volume). In other embodiments, the aqueous sample solution includes about 40% to about 75% acetonitrile (by volume) or about 50% acetonitrile (by volume).

In some embodiments, the test sample and the control sample are aqueous acetonitrile solutions. In some embodiments, the test sample and/or the control sample is an aqueous acetonitrile solution with about a 1:1 volume ratio of water to acetonitrile. In other embodiments, the test sample and/or the control sample is an aqueous acetonitrile solution with about a 1:3 volume ratio of water to acetonitrile. In yet other embodiments, the test sample and/or the control sample is an aqueous acetonitrile solution with about a 3:2 volume ratio of water to acetonitrile.

In some embodiments, such as those in which the amount of $Hg^{2+}$ ions are to be quantified, the methods further include comparing the detected fluorescence of the test sample with the fluorescence of a control sample, wherein a decrease in the fluorescence of the test sample relative to the control sample indicates the presence of $Hg^{2+}$ in the test sample. In some embodiments of the present methods, the control sample includes substantially the same amount of compound of Formula I or II as the test sample but lacks $Hg^{2+}$ ions. By "substantially the same amount of compound" in the present context is meant an amount of compound that is the same or sufficiently similar to the amount used in the test sample to allow measurement of the change in fluorescence due primarily to the binding of the $Hg^{2+}$ ions. It is to be understood that a standard concentration curve may be constructed by measuring the fluorescence of known amounts of $Hg^{2+}$ ions in the presence of the same amount of a compound of Formula I or II. Measurement of the fluorescence of the compound of Formula I or II in a test sample having an unknown amount of $Hg^{2+}$ ions, and comparison to such a standard concentration curve allows for quantification of the $Hg^{2+}$ ions.

The present methods show good to excellent sensitivity in the detection of $Hg^{2+}$ ions. While not wishing to be bound by theory, the sensitivity may result from the fact that compounds of Formula I and II form a 2:1 complex with $Hg^{2+}$ ions. Thus, by use of the proper stoichiometric amounts of the compounds in comparison to $Hg^{2+}$ ions in the sample, relatively large changes in fluorescence may be observed at low mercury concentrations. However, it is not necessary to have the proper stoichiometric amounts of compounds of Formula I or II and $Hg^{2+}$ ions. The present methods can detect the presence of $Hg^{2+}$ when present in excess or in sub-stoichiometric amounts in comparison to the amount of the compound of Formula I or II in the sample. In some embodiments, the present methods can be used to detect $Hg^{2+}$ in the presence of from about 1, up to about 2, up to about 3, up to about 4 and up to about 5 molar equivalents of $Hg^{2+}$ in comparison to the molar amount of a compound of Formula I or II in a sample. In some embodiments, the present method can be used to detect $Hg^{2+}$ with a minimum concentration of about 20 ppb. In some embodiments, the present method can be used to detect $Hg^{2+}$ with a minimum concentration of about 10 ppb or about 20 ppb. In some embodiments, the concentration of $Hg^{2+}$ ion that can be detected in the test sample is at least about 10 ppb; or at least about 15 ppb; or at least about 20 ppb; or at least about 30 ppb; or at least about 40 ppb; or at least about 50 ppb, or at least about 100 ppb in the test sample. In some embodiments, the concentration of $Hg^{2+}$ ion that can be detected is in the range of about 10 ppb to about 100 ppb; or about 15 ppb to about 50 ppb; or about 15 ppb to about 30 ppb; or about 15 ppb to about 25 ppb; or about 20 ppb.

The present methods may also be used to selectively detect $Hg^{2+}$ ion in the presence of one or more different mono- or divalent metal ions. In some embodiments, the methods selectively detect the presence of $Hg^{2+}$ ion in the presence of one or more different monovalent metal ions, including but not limited to monovalent metal ions selected from $Li^+$, $Na^+$, and $K^+$. In some embodiments, the methods selectively detect the presence of $Hg^{2+}$ ion in the presence of one or more different divalent metal ions, including but not limited to divalent metal ions selected from $Ca^{2+}$, $Cd^{2+}$, $Co^{2+}$, $Cr^{2+}$, $Cu^{2+}$, $Fe^{2+}$, $Mg^{2+}$, $Mn^{2+}$, $Ni^{2+}$, $Pb^{2+}$, and $Zn^{2+}$. In the presence of $Hg^{2+}$ ions, significant quenching of the fluorescence emission by the compound of Formula I or II is observed. In contrast, the presence of other divalent metal ions either slightly enhance fluorescence (e.g., $Mg^{2+}$, $Mn^{2+}$ and $Cd^{2+}$) of the test sample or exhibit far less quenching of fluorescence than $Hg^{2+}$.

Sensitivity for mercury is enhanced by the use of aqueous test samples and control samples. By way of illustration only, good results may be obtained with aqueous acetonitrile solutions in which the amount of water by volume ranges from about 25% to about 60%. However, smaller or larger amounts of water may also be used so long as at least a two-fold difference in fluorescence is maintained between $Hg^{2+}$ and the metal ion of interest. It is well within the skill in the art based on the present disclosure to select a suitable volume percentage of water to enhance selectivity of mercury ion detection. Concentrated solutions can be diluted using suitable solvents prior to testing.

In the present methods, the fluorescence of a compound of Formula I or II may be detected by essentially any suitable fluorescence detection device. Such devices typically include a light source for excitation of the fluorophore and a sensor for detecting emitted light. In addition, fluorescence detection devices may contain a means for controlling the wavelength of the excitation light and a means for controlling the wavelength of the light detected by the sensor. Such means are referred to generically as filters and can include diffraction gratings, dichroic mirrors, or filters. Examples of suitable devices include fluorometers, spectrofluorometers and fluorescence microscopes. Many such devices are commercially available from companies such as Perkin-Elmer, Hitachi, Nikon, Molecular Dynamics, or Zeiss. In certain embodiments, the device is coupled to a signal amplifier and a computer for data processing.

Using the above devices, the fluorescence excitation and emission spectra of compounds of Formula I or II may be determined by standard techniques in the art. Thus, suitable excitation and emission wavelengths may be readily selected by those of skill in the art for the application at hand. Generally, compounds of Formula I or II may be excited at a wavelength ranging from about 250 nm to about 400 nm and the emission monitored at wavelength from about 385 nm to about 500 nm (so long as the emission wavelength is longer than the excitation wavelength). For example, compound F may be excited at a wavelength of about 351 nm and monitored at an emission wavelength of about 450 nm.

In some embodiments, metal ion binding by calix[4]arene compounds of the present technology may be detected by alternate techniques including, but not limited to, absorption spectroscopy, ESI mass spectrometry and/or NMR. Examples of absorption spectroscopy techniques that may be used include, but are not limited to, infrared spectroscopy, microwave spectroscopy, and UV-visible spectroscopy.

In some embodiments, the complex species formed between compound of Formula I or II and $Hg^{2+}$ can be isolated and characterized. In some embodiments, the complex species can be characterized using techniques known in the art such as transmission electron microscopy (TEM), atomic force microscopy (AFM), and scanning electron microscopy (SEM) and powder XRD studies. In some embodiments, the binding characteristics of $Hg^{2+}$ towards compounds of Formula I or II can be established based on the DFT computational calculations. In some embodiments, the complex species has a 2:1 ratio of compound of Formula I or II and $Hg^{2+}$.

The compounds of this technology can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis,* 3rd Edition, Wiley, New York (1999), and references cited therein.

Furthermore, the compounds may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this technology, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5, and Supplementals (Elsevier Science Publishers, 1989), Organic Reactions, Volumes 1-40 (John Wiley and Sons, 1991), March's Advanced Organic Chemistry, (John Wiley and Sons, 5$^{th}$ Edition, 2001), and Larock's Comprehensive Organic Transformations (VCH Publishers Inc., 1989).

The compounds of Formula I may be prepared by, for example, the synthetic protocol illustrated Scheme 1. In Scheme 1 the following abbreviations apply: (i) ethyl bromoacetate and base; (ii) dansyl chloride and base; $R^1$ as defined above; $R^{10}$ is $CH_2C(O)OCH_2CH_3$; $OR^{11}$ is a dansyl group; $OR^{12}$ is OH or a dansyl group; and $OR^{13}$ is OH or dansyl group.

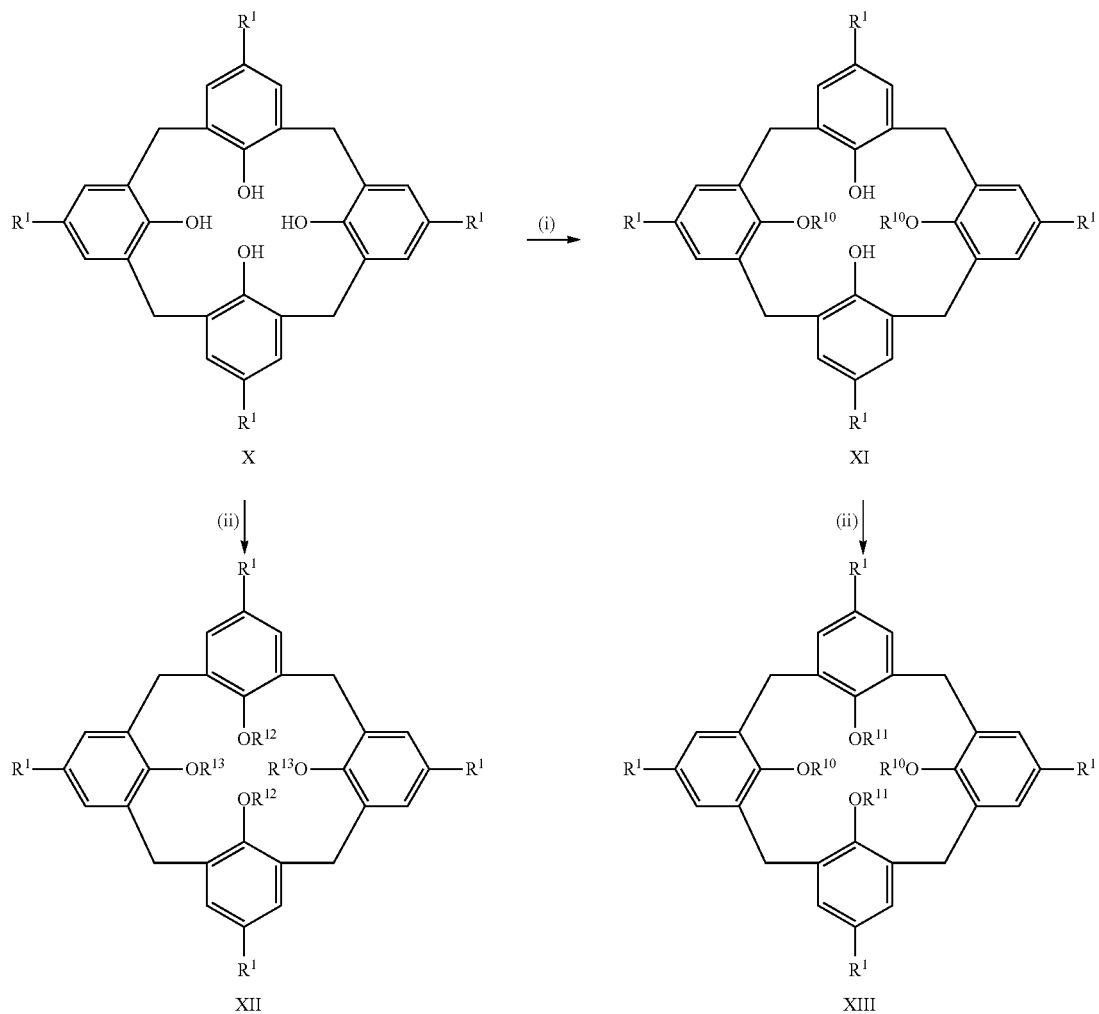

Scheme 1

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or In Scheme 1, the p-Substituted calix[4]arene starting materials X can be purchased from commercial sources or prepared according to the procedure given by Gutsche and co-workers (*J. Am. Chem. Soc.,* 1981, 103, 3782) or by appropriate modification thereof. The compound of Formula X may be reacted with ethyl 2-bromoacetate or similar electrophilic acetates in the presence of a suitable base to produce the ester XI. Example of such bases include, but are not limited to, potassium carbonate, potassium bicarbonate, sodium hydroxide, potassium hydroxide, and the like. The reaction mixture may be heated, e.g., refluxed, if desired.

Hydroxyl compounds X and XI may then be treated with a dansyl halide, in the presence of a base and a solvent to result in the dansyl-substituted calix[4]arenes XII and XIII, which are encompassed by Formula I. The dansyl halides include those of fluoride, chloride, bromide, and iodide. Examples of base include, but are not limited to, tertiary amines or a pyridine compound, such as, triethylamine, diisopropylethylamine, pyridine, and dimethylaminopyridine. Examples of solvent include, but are not limited to, tetrahydrofuran, diethylether, acetonitrile, carbon tetrachloride, dimethyl sulfoxide, dimethylformamide, or dioxane.

Upon reaction completion, each of compounds XI, XII, and XIII can be recovered by conventional techniques such as neutralization, extraction, precipitation, chromatography, filtration, recrystallization and the like. In some embodiments, the compounds are purified using high-performance liquid chromatography. In some embodiments, the compounds are used as is in a subsequent reaction.

It is to be understood that the synthetic method in Scheme I is for illustration purposes only and other deviations or modifications from the scheme that result in the compounds of Formula I are well within the skill of a person of ordinary skill in the art.

The compounds of Formula II may be prepared by, for example, the synthetic protocol illustrated Scheme 2. In Scheme 2 the following abbreviations apply: (iii) $HNO_3$ (100%), glacial acetic acid; (iv) dansyl chloride and base; $R^{11}$ is a dansyl group.

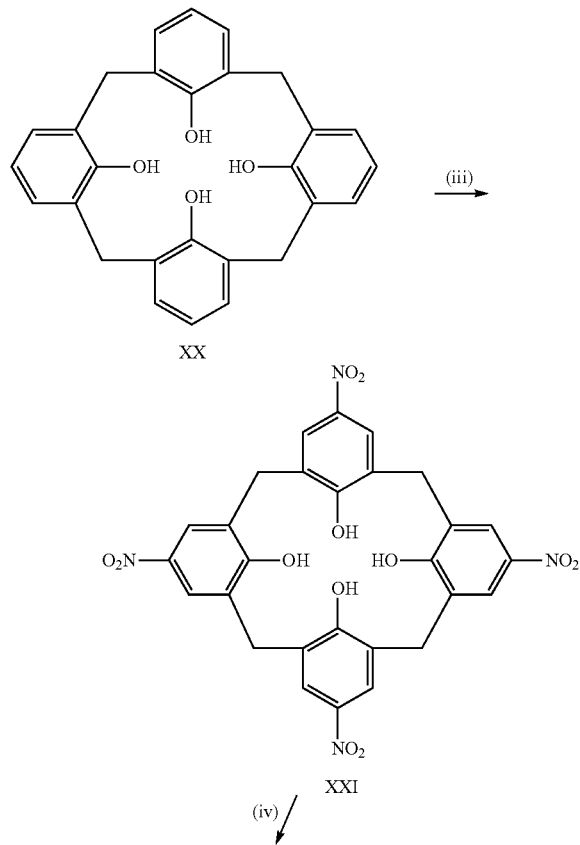

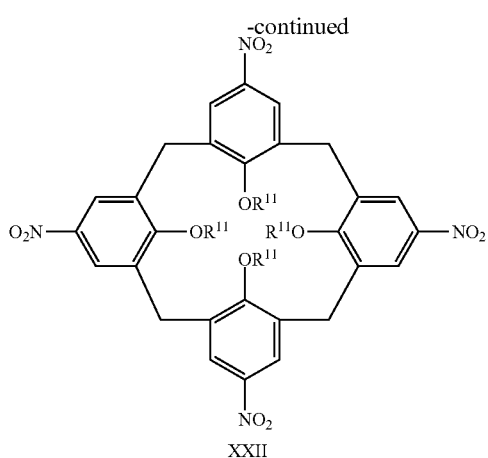

In Scheme 2, the p-calix[4]arene starting material XX can be purchased from commercial sources. The compound of Formula XX may be reacted with nitric acid in the presence of another acid, such as glacial acetic acid to nitrate the starting material, thus forming XXI. The reaction mixture may be cooled, e.g., in an ice bath, if desired.

The hydroxyl XXI may then be treated with a dansyl halide, in the presence of a base and a solvent to result in the dansyl-substituted calix[4]arene of Formula II. The dansyl halides include those of fluoride, chloride, bromide, and iodide. Examples of base include, but are not limited to, tertiary amines or a pyridine compound, such as, triethylamine, diisopropylethylamine, pyridine, and dimethylaminopyridine. Examples of solvent include, but are not limited to, tetrahydrofuran, diethylether, acetonitrile, carbon tetrachloride, dimethyl sulfoxide, dimethylformamide, or dioxane.

Upon reaction completion, each of compounds XXI and II can be recovered by conventional techniques such as neutralization, extraction, precipitation, chromatography, filtration, recrystallization and the like. In some embodiments, the compounds are purified using high-performance liquid chromatography. In some embodiments, the compounds are used as is in a subsequent reaction.

It is to be understood that the synthetic method in Scheme 2 is for illustration purposes only and other deviations or modifications from the scheme that result in the compounds of Formula II are well within the skill of a person of ordinary skill in the art.

Salts of the disclosed compounds are considered within the scope of the present technology. When such compound has a basic group, such as, for example, an amino group, pharmaceutically acceptable salts can be formed with inorganic acids (such as perchloric acid, hydrochloric acid, sulfuric acid, and phosphoric acid), organic acids (e.g., formic acid, acetic acid, citric acid, succinic acid, trifluoroacetic acid, methanesulfonic acid, and p-toluenesulfonic acid) or acidic amino acids (such as aspartic acid and glutamic acid).

EXAMPLES

The present technology is further illustrated by the following examples, which should not be construed as limiting in any way. The following definitions are used herein.

All the reagents used in the study were purchased from Sigma-Aldrich or Merck and were chemically pure. The solvents used were dried and distilled. HPLC grade solvents were used for fluorescence spectroscopic measurements. Column chromatography was performed on silica gel (60-120 mesh) obtained from Merck. $^1H$ and $^{13}C$ NMR spectra were recorded on a 300 MHz Bruker DPX 300 instrument using tetramethylsilane (TMS) at 0.00 as an internal standard. Low temperature $^1$H NMR spectra were also recorded on the same instrument as mentioned above. FAB mass spectra were recorded on a JEOL SX 102/DA-6000 Mass spectrometer/Data System using Argon/Xenon (6 kV, 10 mA) as the FAB gas while IR spectra were recorded on a Nicolet Protégé 460 spectrometer in KBr disks. Fluorescence spectra were acquired on a spectrofluorometer purchased from Horiba-Jobin Yvon, Inc. model FL 3-11 Fluorolog-3 modular spectrofluorometer with single Czerny-Turner grating excitation and emission monochromators having 450 W Xe arc lamp as the excitation source and PMT as the detector. A Perkin-Elmer Lambda bio-20 double beam spectrophotometer with variable bandwidth was used for acquisition of the uv-vis molecular absorbance. All the data were acquired using 1-cm$^2$ path length quartz cuvettes. Spectral response from appropriate blanks was subtracted before data analysis. All the measurements were taken in triplicate and averaged. Dilution correction was also carried out where necessary. Melting points were determined on an electrothermal melting point apparatus obtained from M/S Toshniwal and were uncorrected.

The starting materials p-tert-butylcalix(4)arene; calix(4)arene; 5,11,17,23-tetra(p-tert-butyl)-25,27-di(ethoxycarbonylmethoxy)-26,28-dihydroxy-calix[4]arene; 25,27-di(ethoxycarbonylmethoxy)26,28-dihydroxy-calix[4]arene; and 5,11,17,23-tetranitro-25,26,27,28-tetrahydroxy-calix[4]arene were synthesized as described previously. See Gutsche C. D. et al. *Org. Synth.*, 1990, 68, 234-237; Gutsche, C. D. et al. *J. Org. Chem.*, 1986, 51, 742-745; Creaven, B. S. et al. *Tetrahedron*, 2001, 57, 8883-8887; Verboom, W. et al. *J. Org. Chem.*, 1992, 57, 1313-1316; Kumar, S. et al. *Syn. Commun.*, 2001, 32, 775-779; Kumar, S. et al. *Tetrahedron*, 2004, 60, 1001-1005; Jaime, C. et al. *J. Org. Chem.*, 1991, 56, 3372-3376; Kim, S. et al. *J. Org. Chem.*, 2002, 67, 1372-1375; and Casnati, A. et al. *J. Am. Chem. Soc.*, 1995, 117, 2767-2777.

Example 1

General procedure for the synthesis of dansylated calix(4)arene derivatives. To a solution of the corresponding calix[4]arene (generally designated in Schemes 1 and 2 as compounds X, XI, and XXI) in acetonitrile (20 mL), triethylamine and dansyl chloride (equimolar to per hydroxyl group) were added under $N_2$ atmosphere with vigorous stirring. The reaction mixture was stirred at room temperature for 96 hours. In most cases, a light yellow precipitate formed that was filtered, redissolved in $CHCl_3$, and washed with water and extracted with $CHCl_3$. The organic layer was collected and evaporated to dryness under reduced pressure to yield the dansylated calix(4)arene derivatives as yellow solids that were further purified by column chromatography and recrystallized from $CHCl_3/CH_3OH$.

Compound I-1. Pale yellow solid, yield: 45%, mp 222-224° C.; UV ($\lambda_{max}$, $CH_3CN$): 272. 347 nm. IR (KBr pellet, cm$^{-1}$): 1710, 1577, 1366, 1310, 1259, 1185, 1067. $^1$H NMR (300 MHz, $CDCl_3$, δ in ppm): 8.65 (2H, d, Dan-H), 8.25 (2H, d, Dan-H), 8.09 (2H, d, Dan-H), 7.53 (4H, m, Dan-H), 7.19 (2H, d, Dan-H), 6.74-6.27 (12H, m, ArH), 3.94-3.69 (8H, m, $OCH_2CH_3$ and $OCH_2CO$), 3.36 (d, 4H, $ArCH_2Ar$), 2.89 (s, 12H, $N(CH_3)_2$), 2.52 (d, 4H, $ArCH_2Ar$), 1.25 (t, 6H, $CH_3$). $^{13}$C NMR (75 MHz, $CDCl_3$, δ in ppm): 169.4, 165.6, 156.7, 151.4, 145.4, 135.9, 134.5, 132.3, 131.6, 130.8, 129.5, 128.7, 127.7, 125.3, 123.2, 122.7, 119.8, 115.4, 70.5, 60.8, 45.4, 31.9, 14.2. HRMS (ESI-TOF) m/z: calcd. 1062.7941, found 1062.7570 [M$^+$].

Compound I-2. Pale yellow solid, yield: 60% mp 210-211° C.; UV ($\lambda_{max}$, $CH_3CN$): 272, 348 nm. IR (KBr pellet, cm$^{-1}$): 1761, 1581, 1362, 1304, 1184, 1122, 1065. $^1$H NMR (300 MHz, $CDCl_3$, δ in ppm): 8.62 (2H, d, Dan-H), 8.23 (4H, m, Dan-H), 7.55 (2H, t, Dan-H), 7.39 (2H. t, Dan-H), 7.12 (2H. d, Dan-H), 6.87 and 6.26 (8H, 2 s, Ar—H), 4.72 (s, $OCH_2CO$), 4.26 (q, 4H, $OCH_2CH_3$), 4.23 (d, 4H, $ArCH_2Ar$), 2.88 (s, 12H, $N(CH_3)_2$), 2.62 (d, 4H, $ArCH_2Ar$), 1.35 (t, 6H, $CH_3$), 1.23, 0.73 (2 s, 36H, $C(CH_3)_3$). $^{13}$C NMR (75 MHz. $CDCl_3$, δ in ppm): 169.7, 153.0, 151.2, 147.6, 145.4, 142.6, 133.18, 132.3, 131.3, 129.4, 128.3. 125.9, 124.9, 123.2, 119.8, 115.1, 70.13, 60.5, 45.3, 32.3, 31.5, 14.2. HRMS (ESI-TOF) m/z: calcd. 1309.5933, found 1309.5298 [M$^+$+Na].

Compound I-3. Pale yellow solid, yield: 66%, mp 231-233° C.; UV ($\lambda_{max}$, $CH_3CN$): 272, 355 nm. IR (KBr pellet, cm$^{-1}$): 3571, 1578, 1365, 1307, 1262, 1190, 1083. $^1$H NMR (300 MHz, $CDCl_3$, δ in ppm): 8.59 (2H, d, Dan-H), and 8.47 (2H, d, Dan-H), 8.14 (2H, d, Dan-H), 7.54 (4H, m, Dan-H), 7.14 (2H, d, Dan-H), 6.86 and 6.52 (8H, 2 s, Ar—H), 3.85 (d, 4H, $ArCH_2Ar$), 2.92 (d, 4H, $ArCH_2Ar$), 2.82 (s, 12H, $N(CH_3)_2$), 1.17, 0.74 (2 s, 36H, $C(CH_3)_3$), 1.49 (bs, 2H, OH, $D_2O$ exchangeable). $^{13}$C NMR (75 MHz, $CDCl_3$, δ in ppm): 151.3, 149.9, 149.0, 142.3, 133.0, 131.8, 129.9, 129.3, 127.9, 125.9, 125.0, 122.8, 119.9, 115.9, 45.3, 32.4, 31.5. HRMS (ESI-TOF) m/z: calcd. 1114.5200, found 1114.5498 [M$^+$].

Compound I-4. Pale yellow solid, yield: 56%, mp 271-272° C.; UV ($\lambda_{max}$, $CH_3CN$): 272, 356 nm. IR (KBr pellet, cm$^{-1}$): 3549, 1577, 1365, 1311, 1243, 1184, 1063. $^1$H NMR (300 MHz, $CDCl_3$, δ in ppm): 8.67 (2H, d, Dan-H) and 8.65 (2H, d, Dan-H), 8.18 (2H, d, Dan-H), 7.67 (4H, m, Dan-H), 7.22 (2H, d, Dan-H), 6.93 (d, 4H, Ar—H), 6.64 (8H, m, Ar—H), 3.95 (d, 4H, $ArCH_2Ar$), 3.03 (d, 4H, $ArCH_2Ar$), 2.89 (50 12H, $N(CH_3)_2$), 1.57 (bs, 2H, OH, $D_2O$ exchangeable). $^{13}$C NMR (75 MHz, $CDCl_3$, δ in ppm): 151.3, 149.9, 149.0, 142.3, 133.8, 132.1, 130.2, 129.4, 129.0, 128.6, 126.9, 122.9, 119.5, 116.0, 45.3, 31.5. HRMS (ESI-TOF) m/z: calcd. 891.2774, found 891.2812 [M$^+$].

Compound I-5. Pale yellow solid, yield: 70%, mp 260-262° C.; UV ($\lambda_{max}$, $CH_3CN$): 272, 339 nm. IR (KBr pellet, cm$^{-1}$): 1575, 1366, 1310, 1184, 1133, 1061. $^1$H NMR (300 MHz, $CDCl_3$, δ in ppm): 8.84 (4H, d, Dan-H), 8.81 (4H, d, Dan-H), 8.35 (4H, d, Dan-H), 7.84 and 7.71 (8H, t, Dan-H), 7.38 (4H, d, Dan-H), 7.09 (d, 4H, Ar—H), 6.83 (m, 8H, Ar—H), 4.10 (d, 4H, $ArCH_2Ar$), 3.19 (d, 4H, $ArCH_2Ar$), 3.06 (s, 24H, $N(CH_3)_2$). $^{13}$C NMR (75 MHz. $CDCl_3$, δ in ppm): 152.5, 151.5, 144.7, 133.9, 132.1, 130.2, 129.8, 129.4, 129.0, 128.6. 128.4, 126.9, 122.9, 119.6, 116, 45.4, 31.6. HRMS (ESI-TOF) m/z: calcd. 1356.3717, found 1356.3727 [M$^+$].

Compound II-1. Pale yellow solid, yield: 40%, mp>232° C. (decomp.). UV ($\lambda_{max}$, $CH_3CN$): 272, 347 nm. IR (KBr pellet, cm$^{-1}$): 1579, 1529, 1345, 1261, 1189, 1094, 1026. $^1$H NMR (300 MHz, $CDCl_3$, δ in ppm): 8.78 (4H, d, Dan-H), 8.43 (4H, d, Dan-H), 8.01 (4H, d, Dan-H), 7.81 (4H, t, Dan-H), 7.56 (4H, t, Dan-H), 7.32 (4H, d, Dan-H), 7.58 (8H, s, Ar—H), 3.37 (8H, S, $ArCH_2Ar$), 2.95 (50 24H, $N(C_3)_2$). $^{13}$C NMR (75 MHz, $CDCl_3$, δ in ppm): 152.3, 149.8, 144.7, 134.9, 133.7, 130.9, 130.3, 125.0, 122.9, 118.1, 116.6, 45.4, 34.2. HRMS [ESI-TOF] m/z: calcd. 1538.3276, found 1538.3208 [M$^+$].

Reference Compounds, Example 2

General procedure for the synthesis of reference compounds (1, 2, and 3). To a solution of either p-tert-butylphenol, phenol, or p-nitrophenol in acetonitrile (20 mL), triethylamine and dansyl chloride (1 eq.) was added under $N_2$ atmosphere with vigorous stirring. The reference compounds obtained were further purified by column chromatography and re-crystallized from $CHCl_3/CH_3OH$.

Reference Compound 1: 5-Dimethylamino-naphthalene-1-sulfonic acid 4-tert-butyl-phenyl ester. Pale yellow solid, yield: 80%, mp 95-97° C. UV ($\lambda_{max}$, $CH_3CN$): 272, 352 nm.

IR (KBr pellet, cm$^{-1}$): 1575, 1368, 1302, 1263, 1150, 1065, 1020. $^1$H NMR (300 MHz, CDCl$_3$, δ in ppm): 8.54 (H, d, Dan-H), 8.51 (H, d, Dan-H), 8.04 (H, d, Dan-H), 7.61 (2H, t, Dan-H), 7.41 (2H, t, Dan-H), 7.10 (H, d, Dan-H), 7.19 (2H, d, Ar—H), 6.74 (2H, d, Ar—H), 2.84 (s, 6H, N(CH$_3$)$_2$), 1.15 (s, 9H, C(CH$_3$)$_3$). $^{13}$C NMR (75 MHz, CDCl$_3$, δ in ppm): 151.4, 149.6, 147.0, 131.4, 130.7, 129.3, 126.0, 122.6, 121.6, 119.2, 115.2, 45.1, 34.1. HRMS (ESI-TOF) m/z: calcd. 406.1453, found 406.1446 [M$^-$+Na].

Compound 1

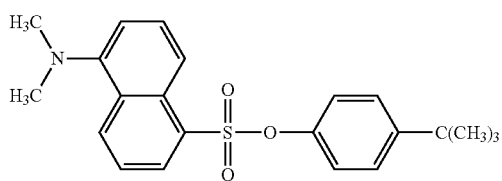

Reference Compound 2: 5-Dimethylamino-naphthalene-1-sulfonic acid phenyl ester. Pale yellow solid, yield: 70%, mp 100-101° C. UV (λ$_{max}$, CH$_3$CN): 272,363 nm. IR (KBr pellet, cm$^{-1}$): 1577, 1365, 1310, 1265, 1143, 1065, 1020. $^1$H NMR (300 MHz, CDCl$_3$, δ in ppm): 8.57 (H, d, Dan-H), 8.38 (H, d, Dan-H), 8.21 (H, d, Dan-H), 7.56 (2H, t, Dan-H), 7.35 (2H, t, Dan-H), 7.09 (H, d, Dan-H), 7.13 (3H, m, Ar—H), 6.72 (2H, m, Ar—H), 2.77 (s, 6H, N(CH$_3$)$_2$). $^{13}$C NMR (75 MHz, CDCl$_3$, δ in ppm): 152.3, 149.8, 144.7, 134.9, 133.7, 130.9, 130.3, 123.2, 122.6, 119.8, 116.2, 45.7. HRMS (ESI-TOF) m/z: calcd. 327.5991, found 327.5912 [M$^+$].

Compound 2

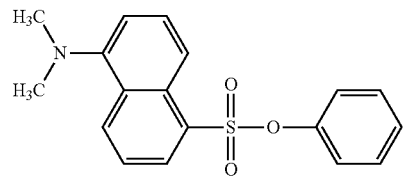

Reference Compound 3: 5-Dimethylamino-naphthalene-1-sulfonic acid 4-nitro-phenyl ester. Pale yellow solid, yield: 85%, mp 98-100° C. UV (λ$_{max}$, CH$_3$CN): 272, 356 nm. IR (KBr pellet, cm$^{-1}$): 1577, 1522, 1345, 1315, 1235, 1175, 1101, 1065. $^1$H NMR (300 MHz, CDCl$_3$, δ in ppm): 8.57 (H, d, Dan-H), 8.36 (H, d, Dan-H), 8.03 (2H, d, Ar—H), 7.65 (2 H, t, Dan-H), 7.39 (2H, t, Dan-H), 7.10 (2H, d, Dan-H), 7.19 (2H, d, Ar—H), 2.84 (s, 6H, N(CH$_3$)$_2$). $^{13}$C NMR (75 MHz, CDCl$_3$, δ in ppm): 153.9, 152.1, 146.0, 132.6, 131.4, 129.4, 125.2, 122.8, 118.8, 115.8, 45.3. HRMS (ESI-TOF) m/z: calcd. 373.5991, found 373.5901 [M$^+$].

Compound 3

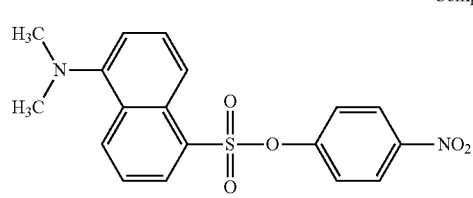

Synthesis And Characterization Of Dansyl-Appended Compounds

As noted above, 5,11,17,23-tetranitro-25,26,27,28-tetrahydroxy-calix[4]arene and calix(4)arene were synthesized according to the reported literature procedure, or purchased. 5,11,17,23-tetra(p-tert-butyl)-25,27-di(ethoxycarbonyl-methoxy)-26,28-dihydroxy-calix[4] arene and 25,27-di(ethoxycarbonylmethoxy)-26,28-dihydroxy-calix[4]arene were synthesized by refluxing the corresponding calix[4]arenes with ethyl bromoacetate in the presence of K$_2$CO$_3$ in acetonitrile for 15 hours.

Calix[4]arene was converted to its tetra-nitro derivative, 5,11,17,23-tetranitro-25,26,27,28-tetrahydroxy-calix[4] arene, via ipso-nitration. The reaction of calix[4]arene and 5,11,17,23-tetranitro-25,26,27,28-tetrahydroxy-calix[4] arene with equimolar amounts per hydroxyl group of the reagents (1:4:4; OH:dansyl chloride:Et$_3$N) resulted in tetra-dansylated derivatives: 25,26,27,28-tetra(N-(5-dimethylaminonaphthalene-1-sulfony))calix[4]arene (compound of Formula I-3) and 5,11,17,23-tetra-nitro-25,26,27-tetra(N-(5-dimethylaminonaphthalene-1-sulfonyl))calix[4]arene (compound of Formula II-1), respectively. Corresponding reactions of 5,11,17,23-tetra(p-tert-butyl)-25,26,27,28-tetrahydroxy-calix[4]arene; calix[4]arene; 5,11,17,23-tetra(p-tert-butyl)-25,27-di(ethoxycarbonylmethoxy)-26,28-dihydroxy-calix[4]arene; and 25,27-di(ethoxycarbonylmethoxy)-26,28-dihydroxycalix[4]arene with dansyl chloride in the presence of triethylamine (Et$_3$N) as base (1:2:2 molar ratio) resulted in di-dansylated calix[4]arene derivatives: 5,11,17,23-tetra-tert-butyl-25,27-bis(N-(5-dimethylaminonaphthalene-1-sulfony))-26,28-dihydroxycalix[4] arene (compound of Formula I-5), 25,27-bis(N-(5-dimethylaminonaphthalene-1-sulfony))-26,28-dihydroxycalix[4]arene (compound of Formula I-2), 5,11,17,23-tetra-tert-butyl-25,27-di(ethoxycarbonyl-methoxy)-26,28-bis(N-(5-dimethylaminonaphthalene-1-sulfony))calix[4] arene (compound of Formula I-4), and 25,27-di(ethoxycarbonyl-methoxy)-26,28-bis(N-(5-dimethylaminonaphthalene-1-sulfony))calix[4]arene (compound of Formula I-1). It is interesting to note that when calix[4]arene is reacted with four equivalents of dansyl chloride and triethylamine, instead of the expected tetra-dansylated product, a di-dansylated derivative of tert-butyl calix[4]arene was obtained. Without being bound to theory, it is speculated that steric hindrance is responsible, due to the presence of four each of tert-butyl and dansyl groups in close proximity. To compare the spectroscopic properties of the dansylated calix[4]arenes, reference compounds 1, 2, and 3 were synthesized by the base-catalyzed acylation of p-tert-butylphenol, phenol, and p-nitrophenol, respectively, with dansyl chloride and triethylamine. These model compounds were further purified by column chromatography and re-crystallized from CHCl$_3$/CH$_3$OH.

The structures of dansylated calix[4]arene derivatives, compounds of Formulas I-1, I-2, I-3, I-4, I-5, and II-1, and Reference Compounds 1, 2, and 3 were established by the analysis of their $^1$H and $^{13}$C NMR spectra as well as MALDI-TOF MS analysis. The $^1$H NMR spectra of the compounds of Formulas I-1, I-2, I-3, I-4, and I-5 show two sets of doublets for the bridging methylene protons. The presence of a pair of doublets for the ArCH$_2$Ar protons in the $^1$H NMR spectra of synthesized dansylated calix[4]arene derivatives (except II-1) and only one signal for methylene carbon in the range of 29-32 ppm in their $^{13}$C NMR spectra suggested that these dansylated calix[4]arene derivatives were in a symmetrical cone conformation in solution. For example, the $^1$H NMR spectrum of IS shows two pairs of doublets for the axial and equatorial protons at 2.92 and 3.85 ppm, respectively, and one distinct signal at 31.5 ppm for the methylene carbon in the $^{13}$C NMR spectrum. The —N(CH$_3$)$_2$ signals appeared at 2.82 ppm in $^1$H NMR and 45.3 ppm in $^{13}$C NMR spectrum. The tert-butyl group was represented by two singlets at 1.17 and 0.74 ppm in $^1$H NMR spectrum and at 32.4 ppm in C$^{13}$ NMR spectrum. All aromatic protons for dansyl group as well as p-tert-butyl-calix[4]arene appeared in the range of 8.59 to 6.52 ppm. The signal for the —OH proton appeared at 1.49 ppm, which is exchangeable with D$_2$O. In contrast, the $^1$H NMR spectrum of the compound of Formula II-1 shows a singlet at 3.37 ppm for the methylene bridged ArCH$_2$Ar protons instead of two pairs of doublets as observed in the case of other dansylated calix[4]arene derivatives. Appearance of a singlet for methylene bridged protons indicates that the compound of Formula II-1 is present in the 1.3-alternate conformation, which is further confirmed by the appearance of one signal at 34.3 ppm in $^{13}$C NMR spectrum. These δ values from NMR results are in good agreement with those reported for other 1,3-alternate compounds.

Temperature-dependent $^1$H NMR was also carried out on the compound of Formula II-1 in CDCl$_3$. From the low-temperature $^1$H NMR spectrum, it is clearly confirmed that the singlet for ArCH$_2$Ar of the compound of Formula II-1 remains as a singlet when the temperature is decreased from +48° C. to −25° C., which is a characteristic of the 1,3-alternate conformation. Existence of the compound of Formula II-1 in the 1,3-alternate instead of the cone conformation may be explained in part on the basis of the steric hindrance due to the presence of four nitro and four dansyl groups; the weak interaction between —NO$_2$ and —N(CH$_3$)$_2$ of the dansyl moiety due to electron-withdrawing nature of NO$_2$ group may contribute to this as well. The different conformation of the compound of Formula II-1 as compared to the other dansyl-appended calix[4]arenes may result in its unique sensing behavior (vide infra).

Dansyl-Appended Calyx[4]Arenes As Fluorescence Chemosensors

Due to the solvatochromic nature of the dansyl-based fluorophores and well-documented host nature of the calix[4] arene framework to which the dansyl moieties are attached, the potential of the dansyl-appended calix[4]arenes as possible fluorescence chemosensing agents for metal ion sensing was explored. For this purpose, dilute solutions of dansyl-appended calix[4]arenes (~10 μM) in acetonitrile (ACN) were excited at an optimum excitation wavelength of 351 nm; the resulting fluorescence was subsequently measured in the presence of varying concentration of metal ions.

As shown in FIG. 1, a significant decrease in fluorescence intensity of the compound of Formula II-1 upon addition of Hg$^{2+}$; a 74% reduction in fluorescence intensity was observed upon addition of 8 μM Hg$^{2+}$. Clearly, the compound of Formula II-1 shows tremendous sensing/recognition ability toward Hg$^{2+}$. If the reduction in the compound of Formula II-1 fluorescence intensity (i,e., $\Delta F=F_0-F$, where $F_0$ and $F$ are the fluorescence intensities in the absence and presence of Hg$^{2+}$, respectively) as up to 8 μM Hg$^{2+}$ is added to the host solution is assumed to vary linearly with [Hg$^{2+}$] (inset FIG. 1), the limit of detection (LOD) for Hg$^{2+}$ can be calculated for the compound of Formula II-1 as a fluorescence chemosensing agent using calibration sensitivity (m) of $\Delta F$ versus [Hg$^{2+}$] in the aforementioned range. For the purpose of LOD calculation, minimum change in the signal ($\Delta F_{min}$) due to the presence of Hg$^{2+}$ was taken to be 3×s$_0$, where s$_0$ is the standard deviation of F$_0$ for twelve replicate measurements. Thus, the LOD is calculated using $LOD_{[Hg^{2+}]}=3\times s_0$, and it is observed to be ~0.1 μM (or ~20 ppb) Hg$^{2+}$. Such low LOD clearly demonstrates the high sensitivity of the compound of Formula II-1 toward Hg$^{2+}$.

Figure 2:
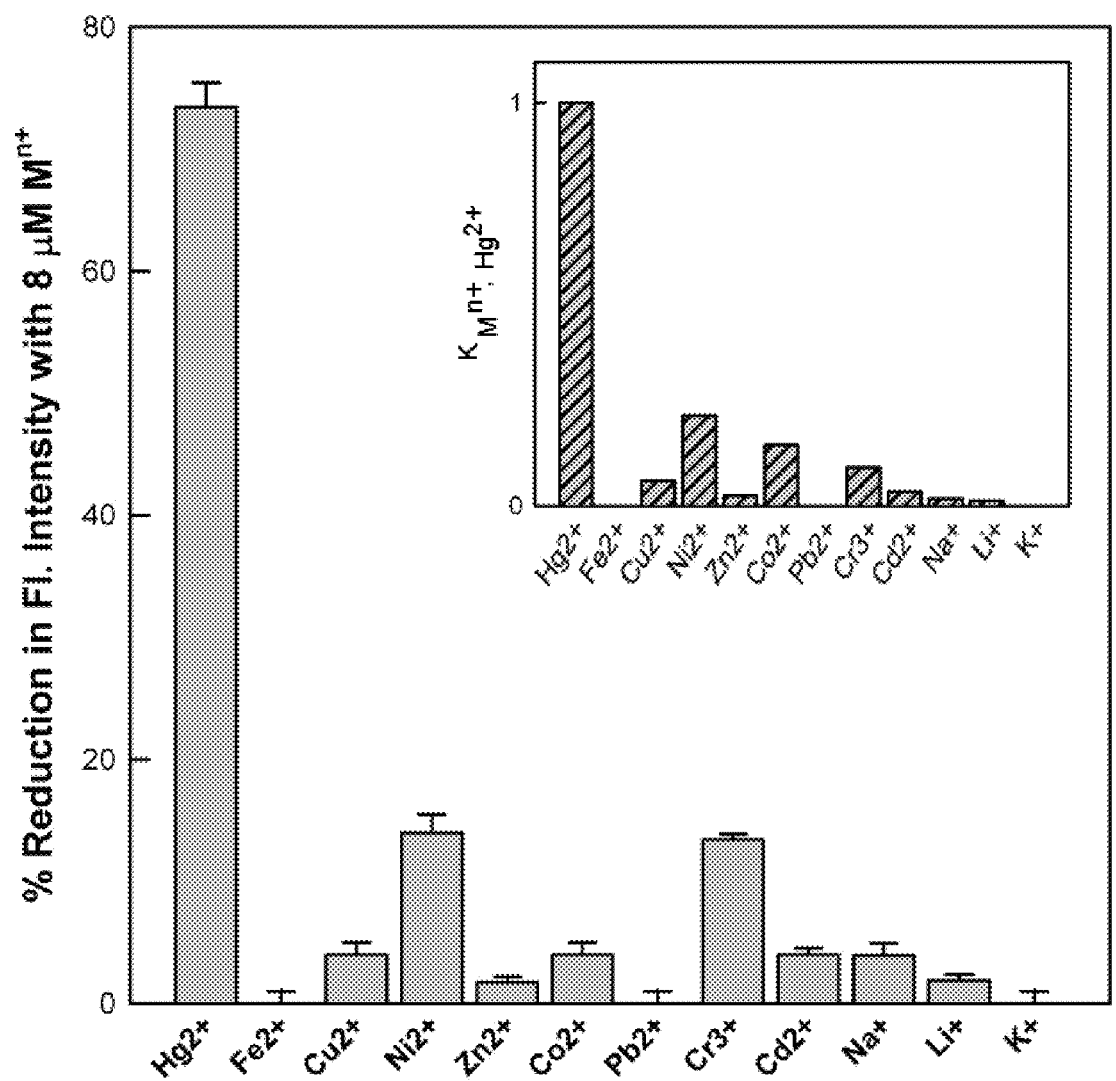
FIG. 2 is a graphic illustration of the percentage reduction in the fluorescence intensity of a compound of Formula II-1 ($1\times10^{-5}$ M) in the presence of 8 μM Mn+ in acetonitrile at ambient conditions ($\lambda_{excitation}$=351 nm). The inset shows the selectivity coefficients for the compound.
Figure 3:
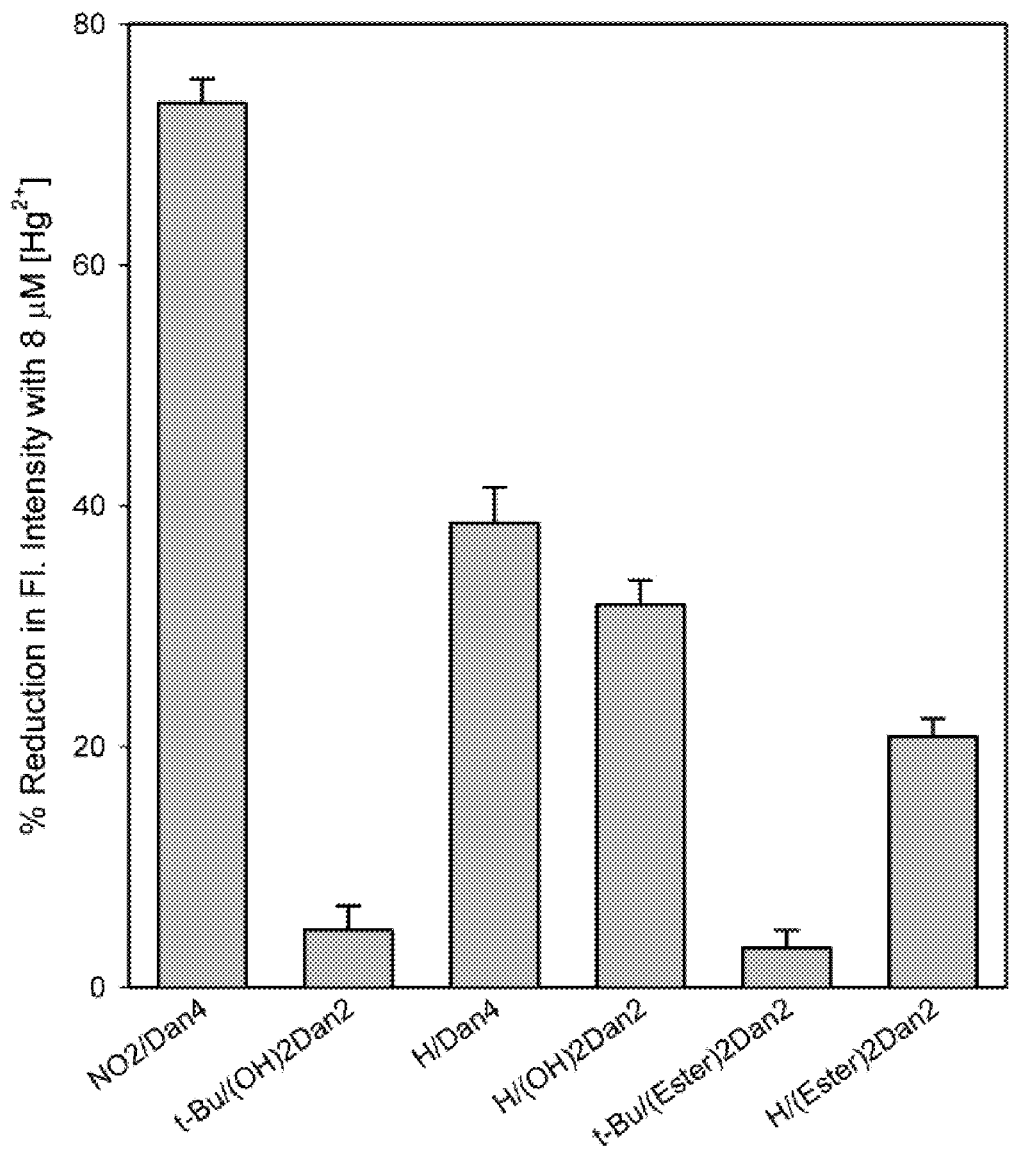
FIG. 3 is a graphic illustration of the percentage reduction in the fluorescence intensity of compounds of the Formulas II-1, I-5, I-3, I-2, I-4, and I-1 (labeled as $NO_2/Dan_4$; t-Bu/$(OH)_2Dan_2$; H/$Dan_4$; H/$(OH)_2Dan_2$; t-Bu/$(Ester)_2Dan_2$; and H/$(Ester)_2Dan_2$, respectively) in the presence of 8 µM $Hg^{2+}$ in acetonitrile at ambient conditions ($\lambda_{excitation}$=351 nm), according to one embodiment.

Changes in fluorescence intensity of the compound of Formula II-1 were then determined in the presence of metal ions other than Hg$^{2+}$, under identical conditions as above (FIG. 2). Although, the fluorescence of the compound of Formula II-1 was severely decreased by Hg$^{2+}$, interestingly, no significant change in the fluorescence intensity the compound of Formula II-1 was observed in the presence of 8 μM Fe$^{2+}$, Cu$^{2+}$, Ni$^{2+}$, Zn$^{2+}$, CO$^{2+}$, Cr$^{3+}$, Cd$^{2+}$, Na$^+$, Li$^+$, and K$^+$, respectively. These results clearly imply the high selectivity of the compound of Formula II-1 toward Hg$^{2+}$ recognition. Selectivity coefficients, $k_{Mn+,Hg2+}=(m_{Mn+}/m_{Hg2+})=(\Delta F_{Mn+})/(\Delta F_{Hg2+})$ were calculated for all metal ions investigated for possible interference. Almost no change in the fluorescence intensity of the compound of Formula II-1 is observed in the presence of Fe$^{2+}$, Pb$^{2+}$, and K$^+$, respectively (FIG. 2), suggesting no interference from these metal ions (i.e., $k_M^{n+}, _{Hg}^{2+}=0$). Values of $k_M^{n+}, _{Hg}^{2+}$ for other metal ions are calculated and plotted in FIG. 2. A careful observation of this data reveals $k_M^{n+}, _{Hg}^{2+}$ for most metal ions to be small enough to pose any significant interference with the detection of Hg$^{2+}$. The reduction in the fluorescence signal of the compound of Formula II-1 by Hg$^{2+}$ in the presence of other metal cations was also measured. The data shows that even in the presence of other metal cations, the efficiency of Hg$^{2+}$ in quenching fluorescence in the compound of Formula II-1 is significant, and in many cases, even similar to that observed in the absence of any other metal cation. These results imply significantly high selectivity associated with the compound of Formula II-1 toward the sensing of Hg$^{2+}$. As shown in FIG. 3, the % reduction in fluorescence intensity upon addition of 8 μM Hg$^{2+}$ was found to be about 38%, 31%, and 20% for the compounds of Formulas I-3, I-2, and I-1, respectively. Thus, the conformational dissimilarity of the compound of Formula II-1 (e.g. a 1,3-alternate conformation, vide supra) with that of other dansyl-appended calix [4]arenes (e.g. cone conformation) to be the reason for this selectivity of the compound of Formula II-1 for Hg$^{2+}$.

To further explore the properties of the compound of Formula II-1 as a chemosensing agent for Hg$^{2+}$, the reversibility of the system was determined. Ethylenediaminetetraacetic acid (EDTA), was used as an external additive, as the formation constant of the EDTA:Hg$^{2+}$ complex is very high ($K_f=6.3\times10^{21}$ at 20° C.). It was observed that the decrease in fluorescence intensity of the compound of Formula II-1 due to the addition of Hg$^{2+}$ was completely recovered by the addition of EDTA of the same concentration as Hg$^{2+}$ (data not shown). Further addition of Hg$^{2+}$ again reduced the fluorescence intensity of the compound of Formula II-1 in the solution. This cycle was repeated several times with the same final outcome. This clearly establishes the reversible nature of the compound of Formula II-1 as a chemosensing agent.

Figure 4:
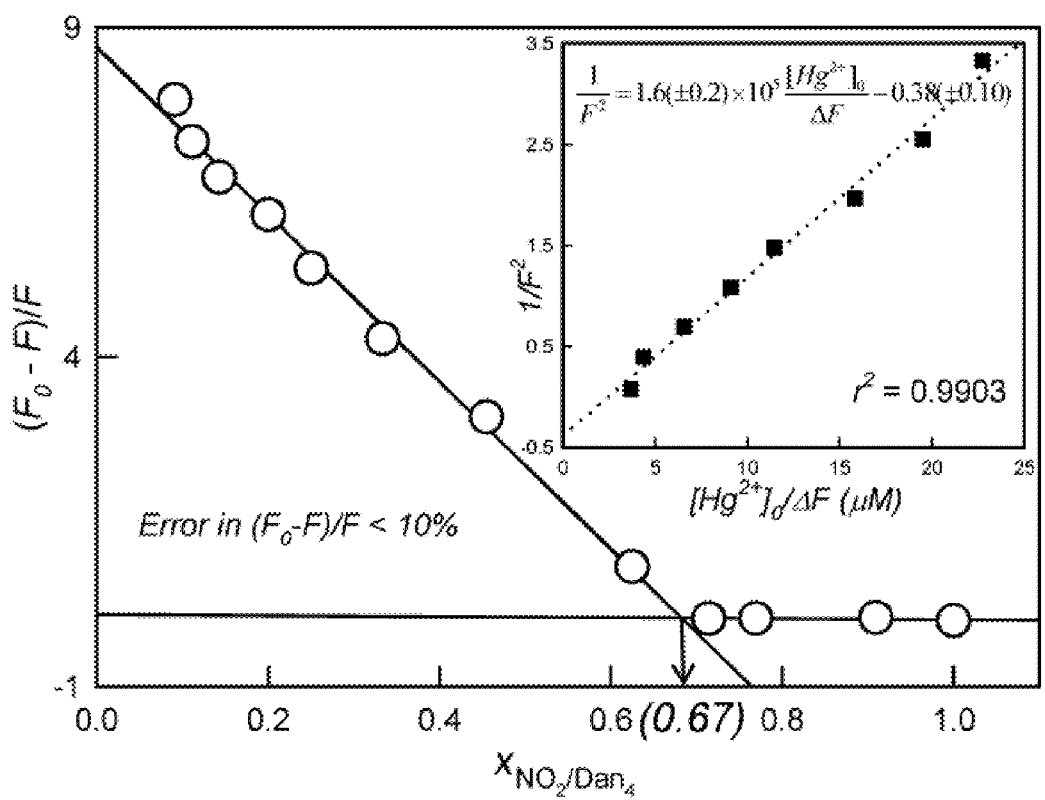
FIG. 4 is a graph of $F_0$–F/F as a function of X (of the compound of Formula II-1, labeled as $X_{NO2/Dan4}$) from the fluorescence reduction of the compound of Formula II-1 in the presence of $Hg^{2+}$ ($\lambda_{excitation}$=351 nm), according to one embodiment. The graph shows that the stoichiometry of the complexation to be 2 compounds of Formula II-1 per one $Hg^{2+}$ at ambient conditions. The inset shows a plot of $1/F^2$ as a function of $[Hg^{2+}]_0/\Delta F$, where $[Hg^{2+}]_0$ is the analytical concentration of $Hg^{2+}$ in the solution.

Stoichiometry and Efficiency of the Compound of Formula I-1: Hg$^{2+}$ Interaction Fluorescence data of the compound of Formula II-1 in the presence of varying [Hg$^{2+}$] (at higher concentration regime) was further analyzed. A detailed Stern-Volmer analysis of the fluorescence data ruled out the possibility of dynamic or static quenching or a combination of both (F$_0$/F versus [Hg$^{2+}$] as well as ((F$_0$/F$_1$)−1)/[Hg$^{2+}$] versus [Hg$^{2+}$]are observed to be far from linear) suggesting interaction or complexation between the compound of Formula II-1 and [Hg$^{2+}$] to be not of the 1:1 type. A plot of Fo-F versus the mole fraction of the host (FIG. 4) clearly shows the stoichiometry of the complexation of the compound of Formula II-1:[Hg2+] to be 2:1.

Fluorescence of Dansyl-Appended Compounds: Relative Fluorescence Intensities

Without being bound by theory, the solvatochromism of dansyl and similar fluorophores appears to be related to (1) the change in fluorophore's dipole moment on optical excitation; and (2) the fact that they possess two excited states; locally excited (LE) and twisted intramolecular charge transfer (TICT). On excitation, the less polar, semi-planar state forms initially, which is very similar in structure to the ground state, giving rise to structured fluorescence spectrum. This LE state can undergo intramolecular electron/charge transfer from the donor site —N(CH$_3$)$_2$ to the acceptor site —SO$_2$— with a corresponding twist of the donor residue about the bond that connects it to the acceptor. Subsequently, in the TICT state, the donor and acceptor are orthogonal to one another, and this state is much more polar in comparison to the LE state. The fluorescence corresponding to this TICT state is usually structure-less and is shifted bathochromically with respect to the LE state. The propensity to form the TICT state and thus shift the spectrum is influenced by the solvent dielectric properties which help to mediate charge transfer and the ability of the donor residue to rotate within the fluorophore. The ability of the donor to rotate depends, in part, on any physical impediments to donor rotation.

Fluorescence emission spectra were recorded for each of the Compounds of Formula I-1, I-2, I-3, I-4, I-5, and II-1 in relatively non-polar CHCl$_3$, polar aprotic ACN, and polar-protic EtOH at ambient conditions (FIG. 5). Most importantly, in the fluorescence data collection, the absorbance of the solutions of different compounds at the excitation wavelength are identical, such that the same number of photons of the given energy is used in the excitation process, irrespective of the identity of the compound. FIG. 5 (left panels) presents fluorescence emission spectra of all the compounds in CHCl$_3$ at ambient conditions. While relative fluorescence is shown in the top panel, the bottom panel presents normalized fluorescence intensity with respect to the highest energy band for each of the compounds. Structured LE fluorescence from dansyl moiety occurs at lower wavelengths while the broad structure-less TICT band appears bathochromically shifted for all the compounds.

EQUIVALENTS

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

Other embodiments are set forth in the following claims.

What is claimed is:

1. A compound having Formula I or Formula II:

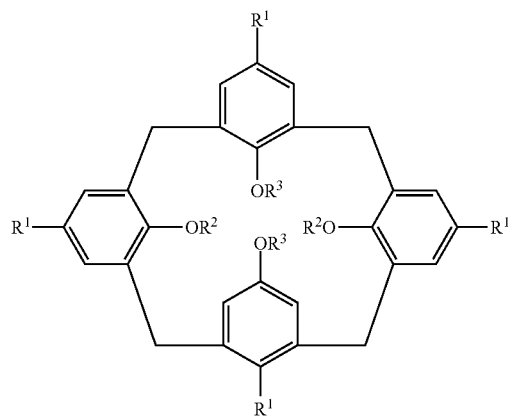

Formula I

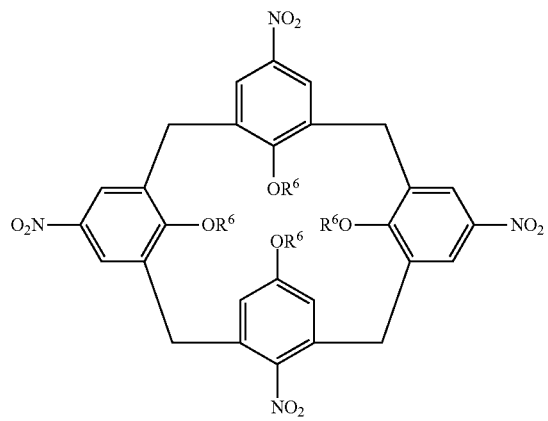

Formula II wherein:
R$^1$ is H, methyl, ethyl, n-propyl, iso-propyl, n-butyl, sec-butyl, tert-butyl, cyclopropyl, cyclobutyl, cyclopentyl or cyclohexyl;
R$^2$ is H, CH$_2$C(O)OR$^4$, or a group of formula

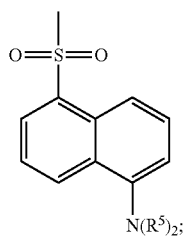

R³ and R⁶ are individually a group of formula

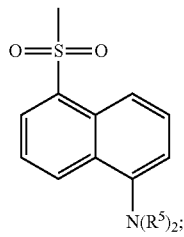

R⁴ is methyl, ethyl, n-propyl, iso-propyl, n-butyl, sec-butyl, or tert-butyl; and R⁵ is methyl, ethyl, n-propyl, iso-propyl, n-butyl, sec-butyl, or tert-butyl.

2. The compound of claim 1 that is Formula I, wherein $R^1$ is H; $R^2$ is $CH_2C(O)OR^4$; $R^4$ is ethyl; and $R^5$ is methyl.

3. The compound of claim 1 that is Formula I, wherein $R^1$ is H; $R^2$ is H; and $R^5$ is methyl.

4. The compound of claim 1 that is Formula I, wherein $R^1$ is H; $R^2$ is a group of formula

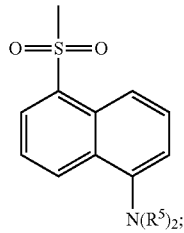

and $R^5$ is methyl.

5. The compound of claim 1 that is Formula I, wherein $R^1$ is tert-butyl; $R^2$ is H; and $R^5$ is methyl.

6. The compound of claim 1 that is Formula I, wherein $R^1$ is tert-butyl; $R^2$ is $CH_2C(O)OR^4$; $R^4$ ethyl; and $R^5$ is methyl.

7. The compound of claim 1 that is Formula II, wherein $R^5$ is methyl.

8. A complex comprising the compound of Formula I or Formula II according to claim 1 and a $Hg^{2+}$ ion.

9. A complex comprising the compound of claim 3 and a $Hg^{2+}$ ion.

10. A complex comprising the compound of claim 5 and a $Hg^{2+}$ ion.

11. A method of testing for the presence of $Hg^{2+}$ comprising:
   detecting the fluorescence of a test sample comprising a compound of claim 1; and
   comparing the detected fluorescence of the test sample to that of a control sample;

wherein:
   a reduction in fluorescence of the test sample relative to the control sample indicates the presence of $Hg^{2+}$ in the sample.

12. The method of claim 11, wherein the method selectively detects the presence of $Hg^{2+}$ in the presence of one or more different divalent metal ions in the sample.

13. The method of claim 12, wherein the one or more different divalent metal ions are selected from the group consisting of $Ca^{2+}$, $Cd^{2+}$, $Co^{2+}$, $Cu^{2+}$, $Fe^{2+}$, $Mg^{2+}$, $Mn^{2+}$, $Ni^{2+}$, $Pb^{2+}$, and $Zn^{2+}$.

14. A method of testing for the presence of $Hg^{2+}$ comprising:
   preparing a test sample comprising a compound of claim 1;
   detecting the fluorescence of the test sample, and
   comparing the detected fluorescence of the test sample to that of a control sample,
   wherein a reduction in fluorescence of the test sample relative to the control sample indicates the presence of $Hg^{2+}$ in the test sample.

15. A method of preparing a compound of Formula I comprising:
   adding a compound of formula $XSO_2R^3$ to a solution of a compound of Formula III, in the presence of a Lewis base;
wherein:

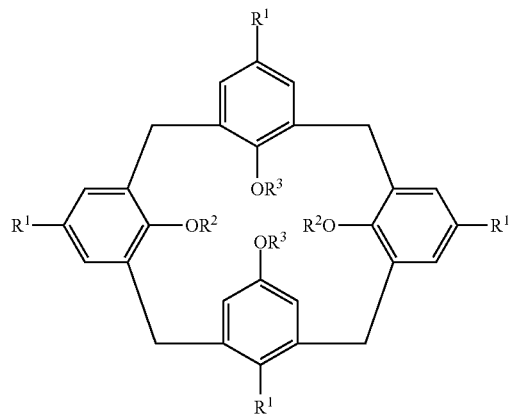

Formula I

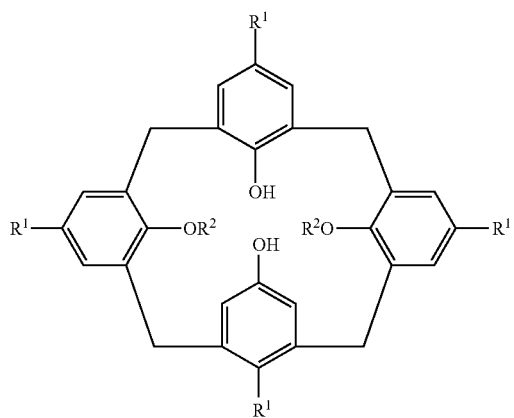

Formula III $R^1$ is H, methyl, ethyl, n-propyl, iso-propyl, n-butyl, sec-butyl, tert-butyl, cyclopropyl, cyclobutyl, cyclopentyl or cyclohexyl;

$R^2$ is H, $CH_2C(O)OR^4$, or a group of formula

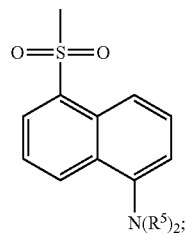

$R^3$ is a group of formula

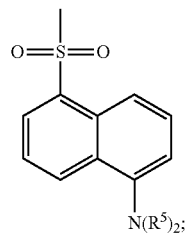

$R^4$ is methyl, ethyl, n-propyl, iso-propyl, n-butyl, sec-butyl, or tert-butyl; and $R^5$ is methyl, ethyl, n-propyl, iso-propyl, n-butyl, sec-butyl, or tert-butyl.

16. The method of claim 15, wherein the Lewis base is a tertiary amine or pyridine.

17. A method of preparing a compound of Formula II comprising:

adding a compound of formula $XSO_2R^3$ to a solution of a compound of Formula IV, in the presence of a Lewis base;

wherein:

Formula II

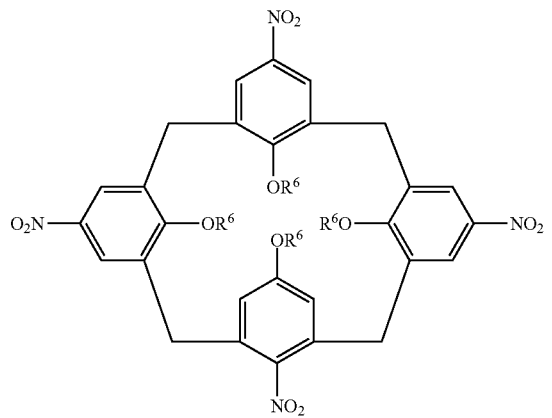

Formula IV

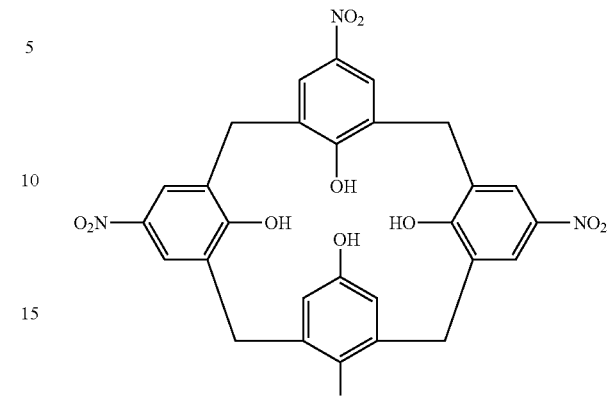

$R^6$ is a group of formula

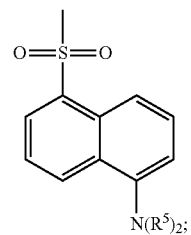

and $R^5$ is methyl, ethyl, n-propyl, iso-propyl, n-butyl, sec-butyl, or tert-butyl.

18. The method of claim 17, wherein the Lewis base is a tertiary amine or pyridine.

19. The method of claim 17, wherein the compound has stereoconformation:

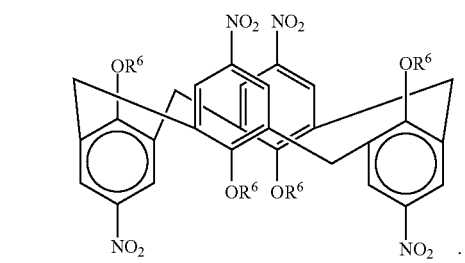

* * * * *

UNITED STATES PATENT AND TRADEMARK OFFICE
CERTIFICATE OF CORRECTION

| | | |
|---|---|---|
| PATENT NO. | : 8,124,416 B2 | Page 1 of 2 |
| APPLICATION NO. | : 12/620126 | |
| DATED | : February 28, 2012 | |
| INVENTOR(S) | : Pandey et al. | |

It is certified that error appears in the above-identified patent and that said Letters Patent is hereby corrected as shown below:

Title Page 2, in Field (56), under "OTHER PUBLICATIONS", in Column 1, Line 43, delete "Chem.." and insert -- Chem. --, therefor.

Title Page 2, in Field (56), under "OTHER PUBLICATIONS", in Column 2, Line 10, delete "Chem.." and insert -- Chem. --, therefor.

Title Page 2, in Field (56), under "OTHER PUBLICATIONS", in Column 2, Line 32, delete "Chem.." and insert -- Chem. --, therefor.

Title Page 2, in Field (56), under "OTHER PUBLICATIONS", in Column 2, Line 48, delete "Butylcallix" and insert -- Butylcalix --, therefor.

Title Page 2, in Field (56), under "OTHER PUBLICATIONS", in Column 2, Line 49, delete "Chem.." and insert -- Chem. --, therefor.

Title Page 2, in Field (56), under "OTHER PUBLICATIONS", in Column 2, Line 60, delete "Chem.." and insert -- Chem. --, therefor.

In Column 4, Line 64, delete "[Hg2+]" and insert -- [$Hg^{2+}$] --, therefor.

In Column 18, Line 26, delete "$CDCl_3$," and insert -- $CDCl_3$, --, therefor.

In Column 20, Line 66, delete "IS" and insert -- I5 --, therefor.

In Column 21, Line 5, delete "$C^{13}$ NMR" and insert -- $^{13}$C NMR --, therefor.

Signed and Sealed this
Twenty-ninth Day of May, 2012

David J. Kappos
*Director of the United States Patent and Trademark Office*

CERTIFICATE OF CORRECTION (continued)
U.S. Pat. No. 8,124,416 B2

In Column 22, Line 15, delete "$k_{Mn+,Hg2+}=(m_{Mn+}/m_{Hg2+})=(\Delta F_{Mn+})/(\Delta F_{Hg2+})$" and insert -- $k_{Mn+,Hg^{2+}}=(m_{Mn+}/m_{Hg^{2+}})=(\Delta F_{Mn+})/(\Delta F_{Hg^{2+}})$ --, therefor.

In Column 22, Line 67, delete "[Hg2+]" and insert -- [$Hg^{2+}$] --, therefor.